US011696901B2

(12) United States Patent
Jing et al.

(10) Patent No.: US 11,696,901 B2
(45) Date of Patent: Jul. 11, 2023

(54) CURCUMIN NANOPARTICLE AND PREPARATION AND APPLICATION THEREOF

(71) Applicant: SHAOGUAN UNIVERSITY, Guangdong (CN)

(72) Inventors: Siqun Jing, Guangdong (CN); Ruimin Zhong, Guangdong (CN); Junyan Zhang, Guangdong (CN)

(73) Assignee: SHAOGUAN UNIVERSITY, Shaoguan (CN)

( * ) Notice: Subject to any disclaimer, the term of this patent is extended or adjusted under 35 U.S.C. 154(b) by 116 days.

(21) Appl. No.: 17/185,913

(22) Filed: Feb. 25, 2021

(65) Prior Publication Data

US 2021/0369644 A1 Dec. 2, 2021

(30) Foreign Application Priority Data

May 28, 2020 (CN) ......................... 202010467969.5

(51) Int. Cl.

| | |
|---|---|
| ***A61K 31/12*** | (2006.01) |
| ***A61K 9/16*** | (2006.01) |
| ***A61K 47/12*** | (2006.01) |
| ***A61K 47/26*** | (2006.01) |
| ***A61K 47/38*** | (2006.01) |
| ***A61K 47/36*** | (2006.01) |
| ***A61K 36/752*** | (2006.01) |
| ***A61K 9/00*** | (2006.01) |
| ***A61K 9/19*** | (2006.01) |
| ***A23L 2/58*** | (2006.01) |
| ***A23L 2/06*** | (2006.01) |
| ***A23L 2/72*** | (2006.01) |
| ***A23L 2/10*** | (2006.01) |
| ***A23L 2/385*** | (2006.01) |
| ***A23L 2/46*** | (2006.01) |
| ***A23L 33/105*** | (2016.01) |
| ***A23L 33/125*** | (2016.01) |
| ***A23L 29/269*** | (2016.01) |
| ***A23L 29/25*** | (2016.01) |
| ***A23L 33/185*** | (2016.01) |
| ***A23L 29/212*** | (2016.01) |
| ***A23L 29/262*** | (2016.01) |
| ***A23L 29/30*** | (2016.01) |
| ***A23L 3/44*** | (2006.01) |

(52) U.S. Cl.

CPC ................ *A61K 31/12* (2013.01); *A23L 2/06* (2013.01); *A23L 2/10* (2013.01); *A23L 2/385* (2013.01); *A23L 2/46* (2013.01); *A23L 2/58* (2013.01); *A23L 2/72* (2013.01); *A23L 3/44* (2013.01); *A23L 29/212* (2016.08); *A23L 29/25* (2016.08); *A23L 29/262* (2016.08); *A23L 29/27* (2016.08); *A23L 29/37* (2016.08); *A23L 33/105* (2016.08); *A23L 33/125* (2016.08); *A23L 33/185* (2016.08); *A61K 9/0095* (2013.01); *A61K 9/1652* (2013.01); *A61K 9/1658* (2013.01); *A61K 9/1694* (2013.01); *A61K 9/19* (2013.01); *A61K 36/752* (2013.01); *A61K 47/12* (2013.01); *A61K 47/26* (2013.01); *A61K 47/36* (2013.01); *A61K 47/38* (2013.01); *A23V 2002/00* (2013.01); *A61K 2236/13* (2013.01); *A61K 2236/15* (2013.01); *A61K 2236/51* (2013.01); *A61K 2236/53* (2013.01)

(58) Field of Classification Search

CPC .... A61K 31/12; A61K 9/0095; A61K 9/1652; A61K 9/1658; A61K 9/1694; A61K 9/19; A61K 36/752; A61K 47/12; A61K 47/26; A61K 47/36; A23L 29/27; A23L 29/262; A23L 33/105; A23L 29/212; A23L 33/125; A23L 29/37; A23L 33/185; A23L 29/25; A23L 2/06; A23L 2/10; A23L 2/385; A23L 2/46; A23L 2/58; A23L 2/72; A23L 3/44

See application file for complete search history.

(56) References Cited

U.S. PATENT DOCUMENTS

2015/0004102 A1 1/2015 Salman et al.

FOREIGN PATENT DOCUMENTS

| | | | |
|---|---|---|---|
| CN | 107712543 | A | 2/2018 |
| CN | 105456196 | B | 12/2018 |
| CN | 110393295 | A | 11/2019 |

OTHER PUBLICATIONS

Chen et al. Evaluation of the colloidal/chemical performance of core-shell nanoparticle formed by zein and gum Arabic. Colloids and Surfaces A 560 (2019): 130-135 (Year: 2019).*

* cited by examiner

*Primary Examiner* — Robert A Wax
*Assistant Examiner* — Olga V. Tcherkasskaya

(57) ABSTRACT

Disclosed is a curcumin nanoparticle, including curcumin as core material and a wall material, where a weight ratio of the curcumin to the wall material is (5.5-7.5):100, and the wall material includes gum arabic and zein in a weight ratio of (1-5):5. The disclosure further provides a method of making the curcumin nanoparticle and a curcumin beverage containing the curcumin nanoparticle.

11 Claims, 9 Drawing Sheets

CURCUMIN NANOPARTICLE AND PREPARATION AND APPLICATION THEREOF

CROSS-REFERENCE TO RELATED APPLICATION

This application claims the benefit of priority from Chinese Patent Application No. 202010467969.5, filed on May 28, 2020. The content of the aforementioned application, including any intervening amendments thereto, is incorporated herein by reference in its entirety.

TECHNICAL FIELD

This application relates to production of functional food, and more particularly to a curcumin nanoparticle and a preparation and application thereof.

BACKGROUND

Curcumin (cur) is a kind of polyphenolic compounds exacted from rhizomes of turmeric, and has a symmetric molecular structure composed of two o-methylated phenols and heptadiene with β-diketone structure. The curcumin powder is yellow-orange, and has a slightly bitter taste. In view of the strong coloring property and low toxicity, the curcumin has been widely applied as a natural pigment in the fields of food, textile and cosmetic. Recently, the curcumin has been demonstrated to have anti-inflammatory, anti-oxidation, anti-neoplastic, anti-depression and antiviral activities, and play an important role in protecting cardiovascular system, repairing brain damage, and relieving symptoms of Parkinson's disease. Unfortunately, the coloring property of the curcumin is not stable enough since it has poor water solubility and is prone to being affected by external factors like temperature, metal ions, pH and light. Particularly under the exposure to natural light, the aqueous curcumin solution is extremely prone to degradation to lose its pharmacological activities and coloring property. In consideration of this, the curcumin is greatly limited in the practical application, especially in the production of liquid food.

SUMMARY

An object of this application is to provide a curcumin nanoparticle and a preparation and application thereof to overcome the above-mentioned defects in the prior art.

Technical solutions of this application are specifically described as follows.

In a first aspect, this application provides a curcumin nanoparticle, comprising:

curcumin as core material; and a wall material;

wherein a weight ratio of the curcumin to the wall material is (5.5-7.5):100; and the wall material comprises gum arabic and zein in a weight ratio of (1-5):5.

In a second aspect, this application provides a method of preparing the curcumin nanoparticle, comprising:

(1) dissolving the zein with 85% ethanol followed by magnetic stirring for 1 h and centrifugation to remove insoluble impurities to produce a zein solution; and adding the curcumin to the zein solution followed by stirring for 30 min to produce a curcumin stock solution;

(2) dissolving gum arabic with a 0.3 g/L zinc sulfate solution at 60° C. under stirring to produce an aqueous gum arabic stock solution, wherein the zinc sulfate solution is prepared by dissolving zinc sulfate with water in a water bath at 60° C., and a volume ratio of water in the aqueous gum arabic stock solution to ethanol in the curcumin stock solution is (1.5-3.5):1;

(3) adding the curcumin stock solution to the aqueous gum arabic stock solution in a trickle manner followed by stirring for 30 min to produce a curcumin nanoparticle dispersion;

(4) concentrating the curcumin nanoparticle dispersion obtained in step (3) by rotary evaporation to obtain a concentrated curcumin nanoparticle dispersion; and (5) subjecting the concentrated curcumin nanoparticle dispersion to freeze drying to produce the curcumin nanoparticle.

In some embodiments, in step (2), the volume ratio of the water in the aqueous gum arabic stock solution to the ethanol in the curcumin stock solution is 3:1.

In some embodiments, a weight ratio of curcumin to the wall material is (5.5-7.5):100, and a weight ratio of the gum arabic to the zein in the wall material is (1-5):5.

In some embodiments, the weight ratio of curcumin to the wall material is 7:100, and the weight ratio of the gum arabic to the zein in the wall material is 4:5.

In a third aspect, this application provides a curcumin beverage, consisting of:

15% by weight of Tribute Citrus concentrate;

0.05%-0.25% by weight of xanthan gum;

0.2%-1% by weight of the curcumin nanoparticle;

0.2%-1% by weight of starch sodium octenyl succinate;

0.05%-0.25% by weight of sodium carboxymethyl cellulose (CMC-Na);

0.1% by weight of citric acid;

10% by weight of xylitol; and water.

In some embodiments, the curcumin beverage consists of:

15% by weight of Tribute Citrus concentrate;

0.15% by weight of xanthan gum;

0.8% by weight of the curcumin nanoparticle;

0.4% by weight of starch sodium octenyl succinate;

0.15% by weight of sodium carboxymethyl cellulose;

0.1% by weight of citric acid;

10% by weight of xylitol; and water.

In a fourth aspect, this application provides a method of preparing the curcumin beverage, comprising:

(1) peeling and coring Tribute Citrus fruits followed by squeezing with a juicer to produce a Tribute Citrus juice; filtering the Tribute Citrus juice twice with a double gauze to collect a filtrate; and concentrating the filtrate by rotary evaporation to a solid content of 70% to produce the Tribute Citrus concentrate;

(2) mixing the curcumin nanoparticle, starch sodium octenyl succinate and the Tribute Citrus concentrate by stirring to obtain a first mixture;

(3) homogenizing the first mixture obtained in step (2) by a homogenizer to obtain a first homogenized product;

(4) compounding the first homogenized product obtained in step (3) with sodium carboxymethyl cellulose, xanthan gum, citric acid and xylitol to produce a second mixture;

(5) homogenizing the second mixture obtained in step (4) by the homogenizer to obtain a second homogenized product;

(6) heating the second homogenized product in a water bath at 80° C. for 15 min followed by degassing to obtain a degassed product; and (7) bottling and sterilizing the degassed product obtained in step (6) to produce the curcumin beverage.

In some embodiments, in step (3), the homogenization is performed at 25 MPa.

In some embodiments, in step (5), the homogenization is performed at 5 MPa.

In some embodiments, in step (7), the sterilization is performed at 121° C. for 10 min.

Compared to the prior art, this application has the following beneficial effects.

1. The curcumin nanoparticle prepared by the method provided herein has significantly enhanced photostability, rendering it suitable as a functional pigment in the production of functional drinks for delaying senescence.

2. The curcumin beverage provided herein can improve the activity of superoxide dismutase (SOD) and reduce the level of malondialdehyde (MDA), showing anti-aging and antioxidant effects.

BRIEF DESCRIPTION OF THE DRAWINGS

This disclosure will be described below with reference to the accompanying drawings for better understanding and implementation of the technical solutions of this disclosure.

DETAILED DESCRIPTION OF EMBODIMENTS

Figure 1:
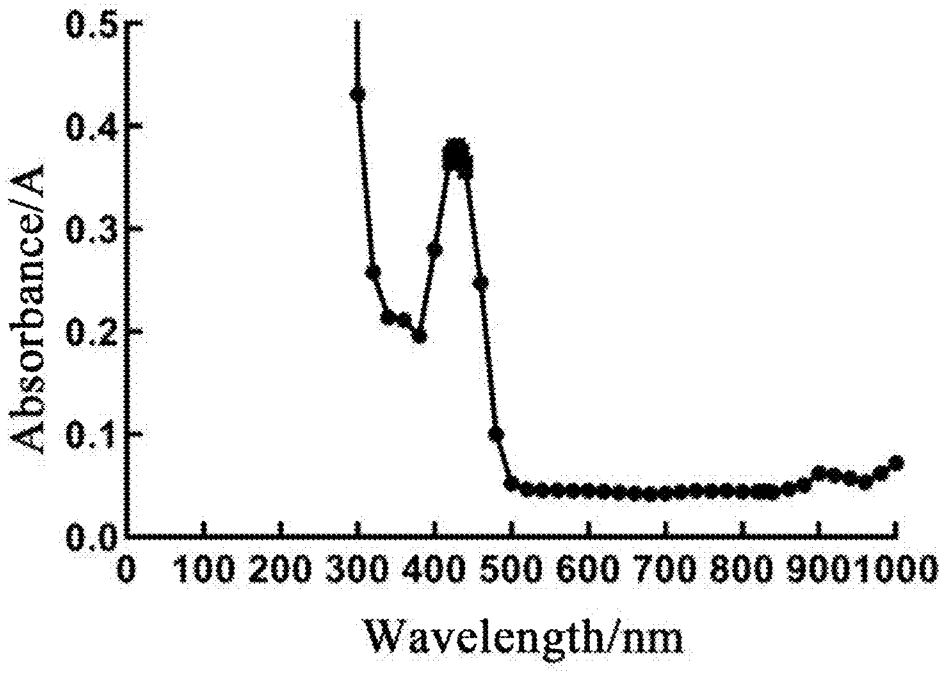
FIG. 1 shows an absorption curve of a curcumin nanoparticle according to Example 1 of this disclosure.
Figure 2:
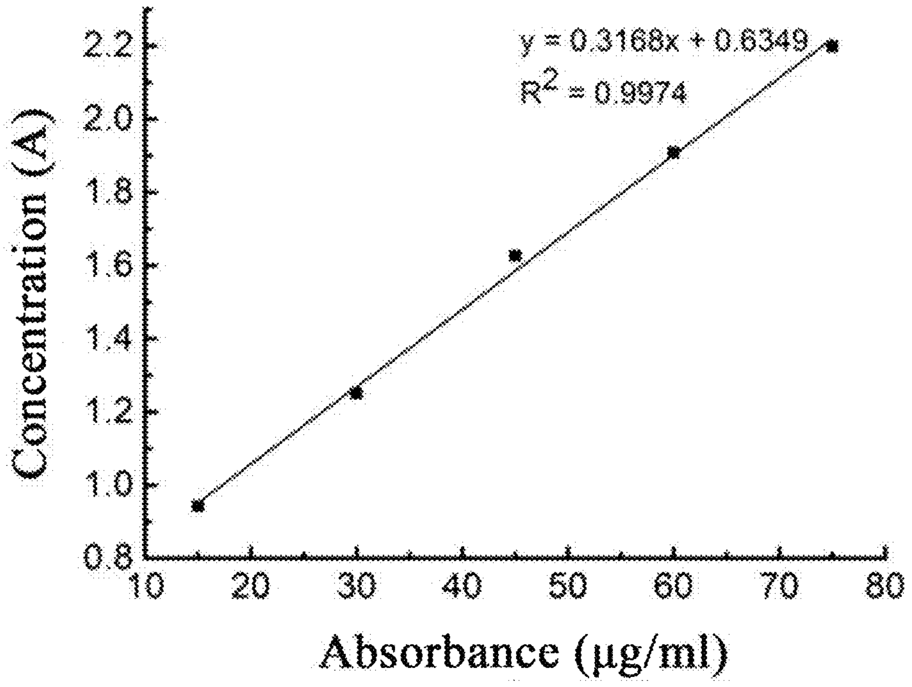
FIG. 2 shows a standard curve of the curcumin nanoparticle according to Example 1 of this disclosure.

Materials and reagents used herein are shown in Table 1.

TABLE 1

| Materials and reagents | | |
|---|---|---|
| Materials and reagents | Grade | Manufacturer |
| Curcumin powder | Food grade (purity 37.98%) | AAFUD Industry (Zhuhai) Co., Ltd |
| Curcumin standard | Primary reference standard (purity 98%) | Shanghai Yuan Mu Biotechnology Co., Ltd. |
| Zein | Food grade | Xinrong Food Ingredients Mall |
| Gum arabic | Food grade | Henan Tanggu Biotechnology Co., Ltd. |
| Zinc sulfate | Analytical grade | Tianjin Fuchen Chemical Reagent Factory |
| Tribute citrus | | Purchased in Shaoguan (Guangdong, China) |
| Xylitol | Food grade | Jiangsu Yangsheng Biotechnology Co., Ltd. |
| Propionic acid | Analytical grade | Xilong Scientific Co., Ltd. |
| CMC-Na | Food grade | Shanghai Shenguang food chemicals Co., Ltd. |
| Starch sodium octenyl succinate | Food grade | Yixing Biotechnology Co., Ltd |
| Methylparaben | Analytical grade | Xilong Scientific Co., Ltd. |
| Xanthan gum | Food grade | Henan Enmiao Food Co., Ltd. |
| Absolute ethyl alcohol | Analytical grade | Tianjin Baishi Chemical Co., Ltd. |
| Ascorbic acid | Analytical grade | Shanghai Yuanye Biotechnology Co., Ltd. |
| DPPH• | Analytical grade | TCI chemical Co., Ltd. |
| Potassium persulfate | Analytical grade | Shanghai Trade Co., Ltd. |
| 2,2'-Azinobis-(3-ethylbenzthiazoline-6-sulphonate) ($ABTS^{+}$•) | Analytical grade | Beijing Solarbio Science & Technology Co., Ltd. |
| Methanol | HPLC grade | Tianjin Damao Chemical Reagent Factory |
| 5% Acetic acid | Analytical grade | Jinan Yuanfeiweiye Chemical Co., Ltd. |
| Absolute ethyl alcohol | Analytical grade | Xilong Scientific Co., Ltd. |
| Ultrapure water | Analytical grade | Jinan Wangsheng Chemical Co., Ltd. |
| Nitric acid | Analytical grade | Shanghai Zhanyun Chemical Co., Ltd. |
| Ebony Flies | | Laboratory of Molecular Biology and Genetics, Sun Yat-sen University |

Instruments used herein are shown in Table 2.

TABLE 2

| Instruments | | |
|---|---|---|
| Instruments | Manufacturer | Model |
| Digital-display thermostatic water bath | Changzhou Yuexin Instrument Manufacturing Co., Ltd. | HH-4 |
| Full wavelength microplate reader | Shanghai Mapada Instruments Co., Ltd. | SHE-3000G |
| Microplate reader | Thermo Fisher Scientific Oy | 1510 |
| Electronic balance | Shanghai Zhuojing Electronic Technology Co., Ltd. | BSM-220.40 |
| Digital-display thermostatic magnetic stirrer | Changzhou Ronghua Instrument Manufacturing Co., Ltd. | JB-3 |
| Low-speed desk centrifuge | Shanghai Anting Scientific Instrument Factory | 800C |
| Freeze dryer | Shanghai Yuming Instrument Co., Ltd. | FD-1E-50 |
| Inductively coupled plasma spectrometer | Thermo Fisher Scientific Inc. | iCAP Q ICP-MS |
| Microwave digestion system | CEM Corporation (US) | MARS6 |
| Laser particle size analyzer | Zhuhai Omec Instruments CO., Ltd. | LS-POP (9) |
| Rotary evaporator | Shanghai Yarong Bio-chemical Instrument Factory | RE-52AA |
| Water circulating vacuum pump | Shanghai Jinfu Experimental instruments Co., Ltd. | SZ-D (III) |
| Experimental homogenizer | Zhengzhou Yuxiang Machinery Equipment Co., Ltd. | CGJB60-70 |
| Steam sterilizer | Guangzhou Hongtu Instruments Co., Ltd | DSX-18L |
| Intelligent light incubator | Shaoguan Guangzhi Technology Equipment Co., Ltd. | GZ-250-GH |
| HPLC | Shimadzu (Suzhou) Co., Ltd. | SPD-16 |
| Food processor | Shandong Joyoung Household Electrical Appliance Co., Ltd. | TYL-350A |

The data processing is performed with the help of GraphPad Prism 7.04, Origin 9, EZ OMNIC and Orthogonal experimental design.

Unless otherwise specified, the materials, reagents and instruments used herein are known in the field to which this application pertains, and are not intended to limit the disclosure. Other suitable reagents and instruments are also feasible.

The curcumin nanoparticle prepared herein and its application will be further illustrated with reference to the following embodiments.

Example 1

Provided herein was a curcumin nanoparticle including a core material and a wall material in a weight ratio of (5.5-7.5):100, where the core material was curcumin, and the wall material was composed of gum arabic and zein in a weight ratio of (1-5):5.

Compared to the prior art, the curcumin nanoparticle provided herein, with curcumin as the core material and a combination of gum arabic and zein as the wall material, has strong light stability and anti-oxidant property in solutions. In addition, the small size renders the curcumin nanoparticle highly water-soluble.

In order to optimize the prepared curcumin nanoparticle, the curcumin material and the mineral composition of curcumin were analyzed as follows.

Analysis of Curcumin Material

The maximum absorption wavelength of curcumin was determined as follows.

0.01 g of curcumin powder was transferred to a 100 mL volumetric flask, and dissolved and diluted with 95% ethanol to 100 mL to produce a 0.1 mg/mL curcumin solution. 500 μL of the 0.1 mg/mL curcumin solution was transferred to another volumetric flask and diluted to 100 mL with 95% ethanol to produce a 0.5 μg/mL curcumin solution. Then the absorbance of the curcumin solution at different wavelengths was measured, and an absorption curve with wavelength as horizontal ordinate and absorbency as vertical ordinate was plotted to obtain the maximum ab sorption wavelength.

As shown in FIG. 1, the maximum absorption wavelength of curcumin was determined to be 425 nm.

A standard curve of curcumin concentration X versus absorbance Y was plotted as follows.

25 mg of curcumin standard was added to a 50 mL volumetric flask, and dissolved and diluted with 95% ethanol to produce a stock solution. The stock solution was diluted to a series of standard solutions respectively with a concentration of 0, 15 μg/mL, 30 μg/mL, 45 μg/mL, 60 μg/mL and 75 μg/mL, which were further measured at 425 nm for the absorbance. The standard curve was plotted based on the curcumin concentration and the corresponding absorbance, and a regression equation of the standard curve was obtained as $Y=0.3168x+0.6349$ ($R^2=0.9974$) by linear fitting.

Analysis of Mineral Composition of Curcumin

The mineral composition of curcumin was analyzed by microwave digestion according to GB 5009.268-2016 “Determination of multiple elements in food”. 0.2824 g of solid curcumin was added to a microwave digestion tube, to which 8 mL of nitric acid was added. The tube was covered with a lid and placed for 1 hour or overnight. Then the lid was screwed tightly and the reaction mixture was subjected to digestion in accordance with the instructions of the microwave digester. After the digestion system was cooled, the lid was slowly opened to release the gas, and the interior lid was rinsed with some water. Then the digestion tube was placed on a temperature-controlled electric hot plate to remove the excessive acid, and the reaction mixture was diluted with ultra-pure water to 25 mL in a volumetric flask and mixed uniformly for use. The same number of blank tests was conducted at the same time.

TABLE 3

| Mineral composition of curcumin | | |
|---|---|---|
| Element | Element content (mg/kg) | Percentage (%) |
| Fe | 11.9382 | 1.19382 |
| Zn | 2.2892 | 0.02892 |

It can be seen from Table 3 that there was a relatively small amount of $Zn^{2+}$ in the curcumin, which will affect the stability of curcumin to some extent.

Determination of optimal concentration of stabilizer ($Zn^{2+}$) A curcumin stock solution was prepared as follows. 0.175 g of curcumin was dissolved with 280 mL of absolute ethanol and stirred thoroughly to prepare the curcumin stock solution.

A series of $Zn^{2+}$ stock solutions were prepared as follows. 0.03 g, 0.06 g, 0.09 g, 0.12 g, 0.15 g and 0.18 g of zinc sulfate were dissolved with 100 mL of distilled water and stirred uniformly to prepare a series of zinc sulfate stock solutions with a concentration of 0.3 g/L, 0.6 g/L, 0.9 g/L, 1.2 g/L, 1.5 g/L and 1.8 g/L, respectively, which were stored for use.

The optimal concentration of Zn' was determined as follows.

The curcumin stock solution was added to 7 vessels each for 40 mL, to which 10 mL of zinc sulfate stock solutions with a concentration of 0.0 g/L, 0.3 g/L, 0.6 g/L, 0.9 g/L, 1.2 g/L, 1.5 g/L and 1.8 g/L was added respectively, that was, the contents of zinc sulfate in the 7 vessels were 0.0 g/L, 0.06 g/L, 0.12 g/L, 0.18 g/L, 0.24 g/L, 0.3 g/L and 0.36 g/L, respectively. The 7 vessels were placed at room temperature and measured for the absorbance at 425 nm using a microplate reader every other 12 h, where each measurement was performed in triplicate.

Figure 3:
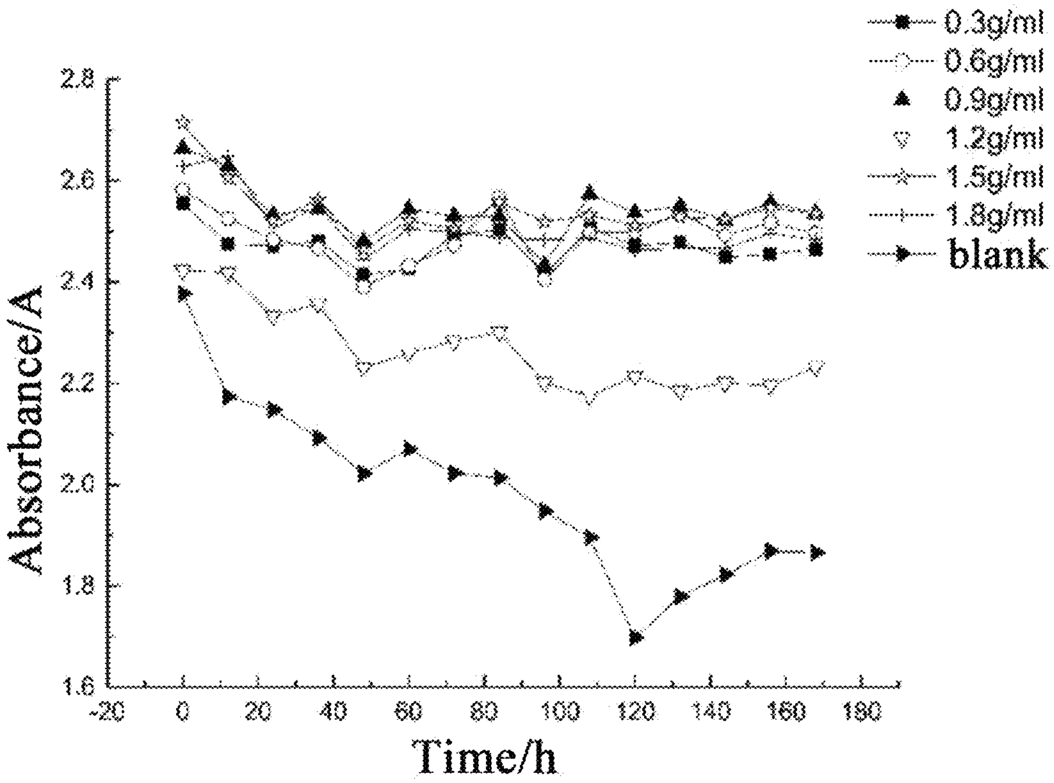
FIG. 3 schematically shows the screening of the optimal concentration of zinc ions according to Example 1 of the disclosure.

As shown in FIG. 3, the curcumin solutions all underwent a fading within 48 h after the addition of different concentrations of zinc ions, while in 48-60 h, the zinc ions resulted in an increase in the absorbance of the curcumin solution. After 60 h, the system with a $Zn^{2+}$ concentration of 0.3 g/L showed the smallest slope and relatively stable absorbance, and by contrast, though the sample with a $Zn^{2+}$ concentration of 0.36 g/L had a relatively stable absorbance, it still exhibited a declining tendency. Therefore, the zinc ions at a concentration of 0.3 g/L can improve the stability of curcumin to the largest extent.

The curcumin nanoparticle of this example was prepared according to the above analysis on the curcumin solid and the mineral composition of curcumin, and the specific preparation process was described as follows.

(1) Preparation of curcumin stock solution

Zein was dissolved in 85% ethanol, magnetically stirred for 1 h and centrifuged to remove the insoluble impurities to obtain a zein solution. Then the zein solution was added with curcumin and stirred for 30 min to produce the curcumin stock solution.

(2) Preparation of gum arabic stock solution

Gum arabic was dissolved with a 0.3 g/L aqueous zinc sulfate solution at a 60° C. water bath under stirring to produce a gum arabic stock solution, where a volume ratio of water in the gum arabic stock solution to ethanol in the curcumin stock solution was (1.5-3.5):1.

(3) Anti-solvent precipitation

The curcumin stock solution was added in a trickle manner into the gum arabic stock solution, and the reaction mixture was stirred for 30 min to produce a curcumin nanoparticle dispersion.

(4) Rotary evaporation

The curcumin nanoparticle dispersion was concentrated by rotary evaporation to obtain a curcumin nanoparticle concentrate.

(5) Drying

The curcumin nanoparticle concentrate was subjected to freeze drying to obtain the curcumin nanoparticle.

The following experiments were conducted to investigate influences of the volume ratio of the water to ethanol, the weight ratio of gum arabic to zein and the weight ratio of curcumin to zein-gum arabic on the prepared curcumin nanoparticle.

Experimental Example 1 Single-Factor Experiment on Preparation of Curcumin Nanoparticle Encapsulation efficiency of the curcumin nanoparticle was used as an index to evaluate the influences of the volume ratio of the water in the gum arabic stock solution to ethanol in the curcumin stock solution, the weight ratio of gum arabic to zein and the weight ratio of curcumin to zein-gum arabic on the prepared curcumin nanoparticle, determining suitable ranges of the above three ratios.

Volume Ratio of Water to Ethanol

The preparation parameters of the curcumin nanoparticle were listed as follows: zein: 1 g; curcumin: 0.02 g; gum Arabic: 1 g; 85% ethanol: 50 mL; 0.3 g/L zinc sulfate solution (calculated based on total volume); and a volume ratio of distilled water to ethanol: 1.5:1, 2:1, 2.5:1, 3:1 and 3.5:1, respectively. The optimal volume ratio of the water to ethanol was determined according to the encapsulation efficiency of the curcumin nanoparticle.

Figure 4:
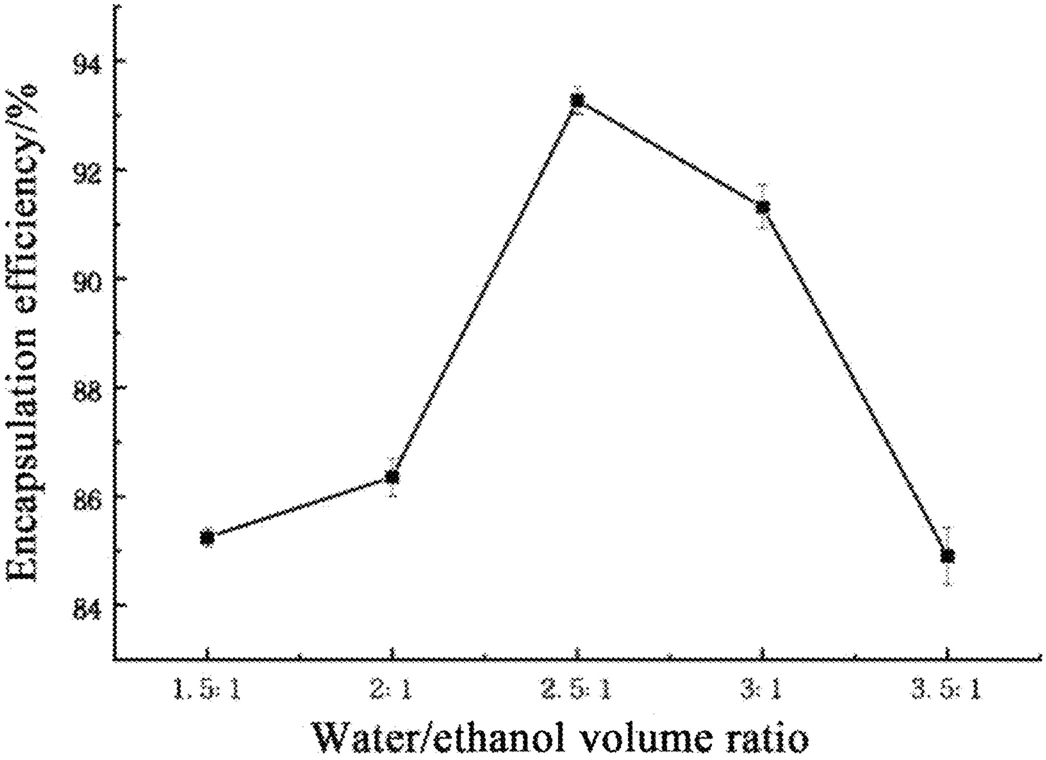
FIG. 4 shows the effect of a water/ethanol volume ratio on the embedding ratio of the curcumin nanoparticle according to Experimental Example 1 of the disclosure.

As shown in FIG. 4, when the volume ratio increased from 1.5:1 to 2.5:1, the encapsulation efficiency of the prepared curcumin nanoparticle was increased from 85.4% to 93.2%; and as the volume ratio increased from 2.5:1 to 3.5:1, the encapsulation efficiency of the prepared curcumin nanoparticle decreased from 93.2% to 84.6%. This phenomenon can be possibly explained by that an increase in the volume ratio of the water to ethanol will lead to the supersaturation of curcumin, so that the curcumin will undergo precipitation during the deposition, bringing a decreased encapsulation efficiency. In view of this, it can be concluded that the optimal volume ratio of the water to ethanol was 2.5:1, and the encapsulation efficiency was always maintained above 84% within the volume ratio range from 1.5:1 to 3.5:1.

Weight Ratio of Gum Arabic to Zein

The preparation parameters of the curcumin nanoparticle were listed as follows: zein: 1 g; curcumin: 0.02 g; distilled water: 75 mL; 85% ethanol: 50 mL; 0.3 g/L zinc sulfate solution (calculated based on total volume); and a weight ratio of gum arabic to zein: 2:10, 4:10, 6:10, 8:10 and 10:10, respectively. The optimal weight ratio of the gum arabic to zein was determined according to the encapsulation efficiency of the curcumin nanoparticle.

Figure 5:
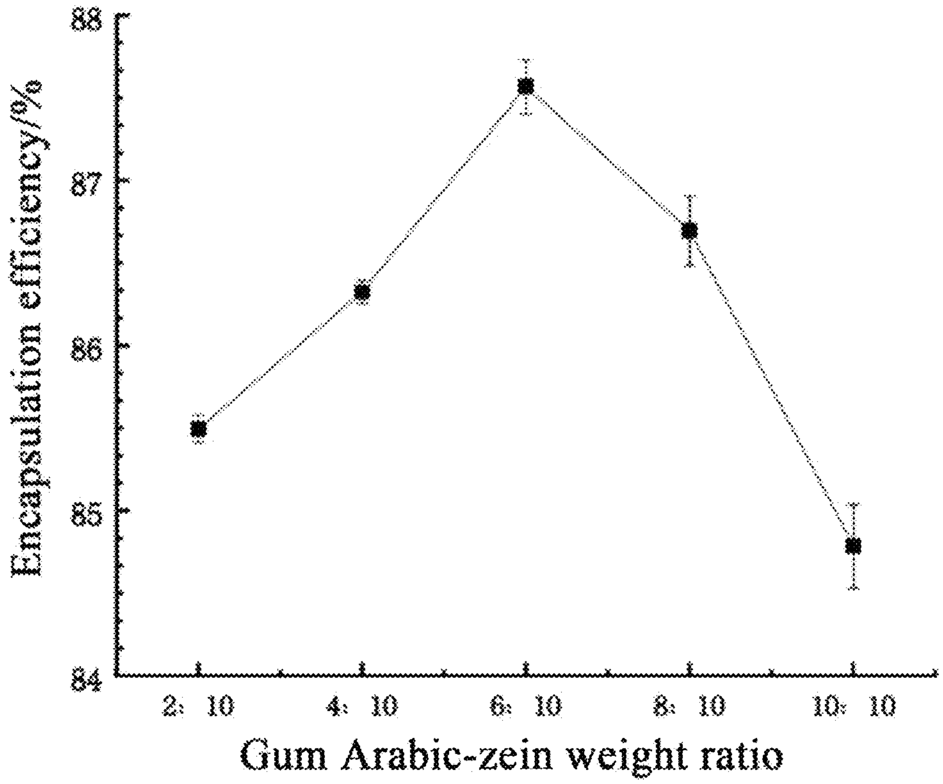
FIG. 5 shows the effect of a gum arabic/zein weight ratio on the embedding ratio of the curcumin nanoparticle according to the Experimental Example 1 of the disclosure.

As shown in FIG. 5, as the weight ratio increased, the encapsulation efficiency of the prepared curcumin nanoparticle first increased and then decreased. The encapsulation efficiency reached its peak (87.1%) at a weight ratio of 6:10, which could probably due to the complete neutralization of the charges of gum arabic and zein. The following decrease in the encapsulation efficiency resulted from the charge imbalance. The optimal weight ratio of gum arabic to zein was determined to 6:10. Further, the encapsulation efficiency was always maintained above 84% within the weight ratio range from 2:10 to 10:10.

Weight Ratio of Curcumin to Gum Arabic-Zein

The preparation parameters of the curcumin nanoparticle were listed as follows: zein: 1 g; gum arabic: 1 g; distilled water: 75 mL; 85% ethanol: 50 mL; 0.3 g/L zinc sulfate solution (calculated based on total volume); and a weight ratio of curcumin to gum arabic-zein: 5.5:100, 6:100, 6.5:100, 7:100 and 7.5:100, respectively. The optimal weight ratio of the curcumin to gum arabic-zein was determined according to the encapsulation efficiency of the curcumin nanoparticle.

Figure 6:
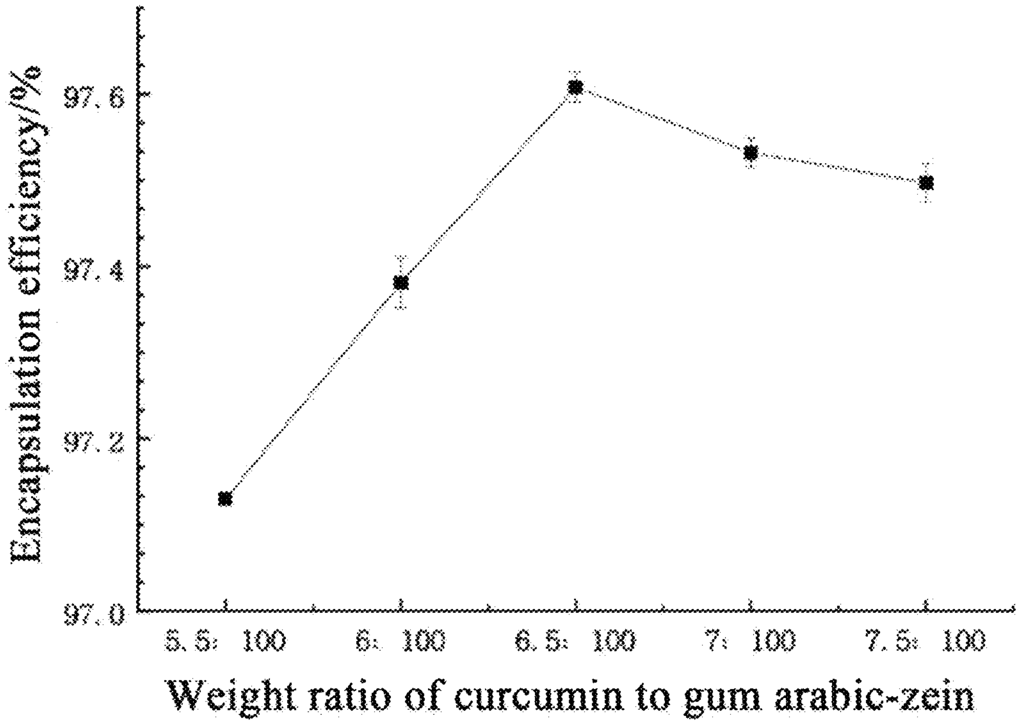
FIG. 6 shows the effect of a weight ratio of curcumin to a combination of gum arabic and zein on the embedding ratio of the curcumin nanoparticle according to the Experimental Example 1 of the disclosure.

As shown in FIG. 6, when the weight ratio increased from 5.5:100 to 6.5:100, the encapsulation efficiency of the prepared curcumin nanoparticle was improved from 97.1% to 97.6%; and when the weight ratio increased from 6.5:100 to 7.5:100, the encapsulation efficiency of the prepared curcumin nanoparticle decreased. It is probable that at a weight ratio of 6.5:100, the load of wall material reached the maximum, and the subsequent increase in the weight ratio will lead to an increase in the amount of free curcumin, reducing the encapsulation efficiency. The optimal weight ratio of curcumin to gum arabic-zein was determined to 6.5:100. Further, the encapsulation efficiency was always maintained above 97% within the weight ratio range from 5.5:100 to 7.5:100.

Furthermore, an orthogonal experiment was designed to determine the optimal volume ratio of the water to ethanol, the optimal weight ratio of gum arabic to zein and the optimal weight ratio of curcumin to zein-gum Arabic.

Specifically, the above three factors (i.e., the volume ratio of the water and ethanol, the weight ratio of gum arabic to zein and the weight ratio of curcumin to zein-gum Arabic) were optimized using the following $L_9(3^4)$ orthogonal table (Table 4), where encapsulation efficiency, light stability (expressed by light stability score=(1−(At−$A_1$)/At)) and particle size (expressed by particle size score=(1-particle size)) were used as indexes to perform multi-index comprehensive evaluation. Higher light stability score and particle size score indicated more desirable results, and the light stability score was directly associated with the retention rate.

TABLE 4

$L_9(3^4)$ orthogonal table of the preparation of curcumin nanoparticle

| Level | Factor: A Volume ratio of the water to ethanol | B Weight ratio of ingredients of wall material | C Weight ratio of core material to wall material |
|---|---|---|---|
| 1 | 2:1 | 4:10 | 6:100 |
| 2 | 2.5:1 | 6:10 | 6.5:100 |
| 3 | 3:1 | 8:10 | 7:100 |

Measurement of Encapsulation Efficiency of Curcumin Nanoparticle 1 mL of the curcumin nanoparticle was dispersed in 4 mL of 95% ethanol in a beaker, and subjected to ultrasonic extraction for 15 min to obtain free curcumin. Then the extraction system was filtered with 0.22 μm organic filter. The extraction was repeated three times, and the extracts were combined and measured at 425 nm for the absorbance, where the blank control was 95% ethanol. Then the obtained absorbance was plugged into the standard curve of curcumin in 95% ethanol to calculate the amount of free curcumin. The encapsulation efficiency and loading amount were calculated according to the following equations:

Encapsulation efficiency/(%)=(addition amount of curcumin-amount of free curcumin)/addition amount of curcumin×100%; and Loading amount/(mg/g)=(addition amount of curcumin×encapsulation efficiency×1000)/(a total weight of zein and gum arabic+addition amount of curcumin).

Measurement of Particle Size of Curcumin Nanoparticle

The prepared curcumin nanoparticle was diluted, placed in a sample pool and measured by a laser particle analyzer for the particle size.

Investigation on light stability of curcumin nanoparticle

The prepared curcumin nanoparticle was diluted 4 times, placed at room temperature and measured by the microplate reader for the absorbance every 24 h to observe the influence of encapsulation on the light sensitivity of curcumin, where the unencapsulated curcumin was used as blank control. Curves of retention rates (calculated by $\ln(A_t^*/A_1^*)$) of the zein-gum arabic-curcumin nano-system and the unencapsulated curcumin versus time were respectively plotted to observe the influence of encapsulation on the light sensitivity of curcumin.

In the equation, $A_t$ represented the absorbance of sample at different time points at room temperature; and $A_1$ represented the initial absorbance.

Figure 7:
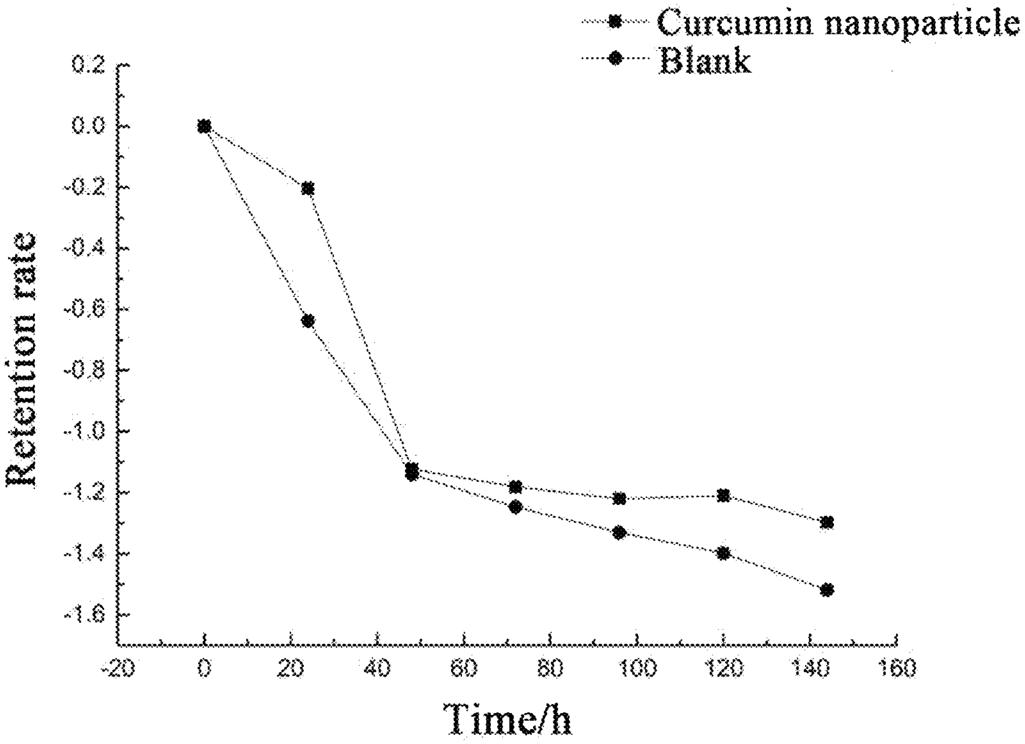
FIG. 7 shows the comparison between the curcumin nanoparticle and curcumin standard in terms of curcumin retention rate under natural light according to Experimental Example 1 of the disclosure.

It can be observed from FIG. 7 that after 48 h, the retention rate of the curcumin nanoparticle (prepared under the optimal conditions) tended to be stable, and the retention rate of the encapsulated curcumin was larger than that of the unencapsulated curcumin. Therefore, the encapsulation significantly inhibited the photodegradation of curcumin, allowing for enhanced light stability.

Results of the orthogonal experiment were shown in Table 5.

TABLE 5

Results of the $L_9(3^4)$ orthogonal experiment

| Test number | Factor: A Volume ratio of the water to ethanol | B Weight ratio of ingredients of wall material | C Weight ratio of core material to wall material | Blank column | Light stability score | Encapsulation efficiency (%) | Particle size score |
|---|---|---|---|---|---|---|---|
| 1 | 1 (2:1) | 1(4:10) | 1 (6:100) | 1 | 0.32 | 95.179 ± 0.02 | −0.717 |
| 2 | 1 (2:1) | 2(6:10) | 2 (6.5:100) | 2 | 0.19 | 96.191 ± 0.05 | −0.729 |
| 3 | 1 (2:1) | 3(8:10) | 3 (7:100) | 3 | 0.27 | 96.730 ± 0.02 | 0.060 |
| 4 | 2 (2.5:1) | 1(4:10) | 2 (6.5:100) | 3 | 0.34 | 94.298 ± 0.02 | −0.015 |
| 5 | 2 (2.5:1) | 2(6:10) | 3 (7:100) | 1 | 0.23 | 95.426 ± 0.03 | 0.354 |
| 6 | 2 (2.5:1) | 3(8:10) | 1 (6:100) | 2 | 0.33 | 96.156 ± 0.04 | 0.105 |
| 7 | 3 (3:1) | 1(4:10) | 3 (7:100) | 2 | 0.49 | 93.708 ± 0.02 | 0.175 |
| 8 | 3 (3:1) | 2(6:10) | 1 (6:100) | 3 | 0.40 | 94.735 ± 0.06 | 0.050 |
| 9 | 3 (3:1) | 3(8:10) | 2 (6.5:100) | 1 | 0.36 | 95.844 ± 0.02 | 0.004 |

TABLE 5-continued

Results of the $L_9(3^4)$ orthogonal experiment

| Test number | Factor A Volume ratio of the water to ethanol | Factor B Weight ratio of ingredients of wall material | Factor C Weight ratio of core material to wall material | Blank column | Light stability score | Encapsulation efficiency (%) | Particle size score |
|---|---|---|---|---|---|---|---|
| $k_1$ | 0.260 | 0.383 | 0.350 | 0.303 | | | |
| $k_2$ | 0.300 | 0.273 | 0.297 | 0.337 | | | |
| $k_3$ | 0.417 | 0.350 | 0.330 | 0.337 | | | |
| Range | 0.157 | 0.110 | 0.053 | 0.034 | | | |
| Primary and secondary factor | A > B > C | | | | | | |
| Optimal combination | $A_3B_1C_1$ | | | | | | |
| $k'_1$ | 96.033 | 94.395 | 95.357 | 95.483 | | | |
| $k'_2$ | 95.293 | 95.451 | 95.444 | 95.352 | | | |
| $k'_3$ | 94.762 | 96.243 | 95.288 | 95.254 | | | |
| R' | 1.271 | 1.848 | 0.156 | 0.229 | | | |
| Primary and secondary factor | B > A > C | | | | | | |
| Optimal combination | $B_3A_1C_2$ | | | | | | |
| $k''_1$ | −0.462 | −0.231 | −0.187 | −0.120 | | | |
| $k''_2$ | 0.103 | −0.108 | −0.292 | −0.150 | | | |
| $k''_3$ | 0.076 | 0.056 | 0.196 | −0.013 | | | |
| R'' | 0.565 | 0.287 | 0.488 | 0.137 | | | |
| Primary and secondary factor | A > C > B | | | | | | |
| Optimal combination | $A_2C_3B_3$ | | | | | | |

The results of variance analysis of the indexes were presented in Tables 6-9.

TABLE 6

Results of variance analysis based on encapsulation efficiency

| Index | Factor | Sum of squares | Degree of freedom | Divided differences | F value | Significance | Critical value of F-test |
|---|---|---|---|---|---|---|---|
| Encapsulation efficiency | A | 2.445 | 2 | 1.222 | 30.949 | * | $F_{0.05}(2, 2) = 19.00$ |
| | B | 5.159 | 2 | 2.580 | 65.304 | * | $F_{0.10}(2, 2) = 9.00$ |
| | C | 0.040 | 2 | 0.020 | 0.468 | | |
| | e | 0.079 | 2 | 0.039 | | | |

TABLE 7

Results of variance analysis based on particle size

| Index | Factor | Sum of squares | Degree of freedom | Divided differences | F value | Significance | Critical value of F-test |
|---|---|---|---|---|---|---|---|
| Particle size score | A | 0.610 | 2 | 0.305 | 19.677 | * | $F_{0.05}(2, 2) = 19.00$ |
| | B | 0.124 | 2 | 0.062 | 4.000 | | $F_{0.10}(2, 2) = 9.00$ |
| | C | 0.396 | 2 | 0.198 | 12.774 | | |
| | e | 0.031 | 2 | 0.0155 | | | |

TABLE 8

Results of variance analysis on degradation rate of absorbance

| Index | Factor | Sum of squares | Degree of freedom | Divided differences | F value | Significance | Critical value of F-test |
|---|---|---|---|---|---|---|---|
| Light stability score | A | 0.040 | 2 | 0.020 | 20.000 | * | $F_{0.05}(2, 2) = 19.00$ |
| | B | 0.018 | 2 | 0.009 | 9.000 | | $F_{0.10}(2, 2) = 9.00$ |
| | C | 0.004 | 2 | 0.002 | 2.000 | | |
| | e | 0.002 | 2 | 0.001 | | | |

Note:
* represents significance $p < 0.05$.

TABLE 9

Optimal combination for each index

| Index | Light stability score | Encapsulation efficiency | Particle size score |
|---|---|---|---|
| Significance | A (statistically significant) | A and B (statistically significant) | A (statistically significant) |
| R value | A>B>C | B>A>C | A>C>B |
| Optimal combination | $A_3B_1C_1$ | $B_3A_1C_2$ | $A_2C_3B_3$ |

It can be seen from Tables 5-9 that the factor A could significantly influence the light stability, encapsulation efficiency and particle size. According to R value, $A_3$ was optimal when the light stability was used as the index; $A_1$ was optimal when the encapsulation efficiency was used as the index; and $A_2$ was optimal when the particle size was used as the index. Factor B had a significant influence on the encapsulation efficiency, and $B_3$ was selected in view of the R value. Factor C had no significant influence on all of the three indexes, but considering that the particle size of the nanoparticle was required to be relatively small and the R value, $C_3$ was preferred. Further, the optimal level for the preparation of curcumin particle was determined as $A_3B_3C_3$ by comprehensive balancing method, that was, the volume ratio of the water to ethanol was 3:1; the weight ratio of gum arabic to zein was 8:10; and the weight ratio of curcumin to zein-gum arabic was 7:100. It was further confirmed by experiments that the curcumin nanoparticle prepared under optimal conditions had an encapsulation efficiency of 95.884%, a loading amount of 62 mg/g, a particle size of 0.940 μm, and an absorbance descending slope of 0.73.

Example 2

Provided herein was a curcumin beverage, consisting of:
15% by weight of Tribute Citrus concentrate;
0.05%-0.25% by weight of xanthan gum;
0.2%-1% by weight of the curcumin particle;
0.2%-1% by weight of starch sodium octenyl succinate;
0.05%-0.25% by weight of CMC-Na;
0.1% by weight of citric acid;
10% by weight of xylitol; and
water.

Specifically, the addition of 0.2%-1% by weight of the curcumin nanoparticle made the curcumin beverage have activities of improving the activity of superoxide dismutase (SOD) and reducing the level of malondialdehyde (MDA), showing anti-aging and antioxidation effects.

Preparation of the Curcumin Beverage (1) Preparation of Tribute Citrus concentrate Tribute Citrus fruits were cored and peeled, and then squeezed with a juicer to produce a Tribute Citrus juice, which was filtered twice with a double gauze to collect a filtrate. The filtrate was concentrated by rotary evaporation to a solid content of 70% to produce the Tribute Citrus concentrate.

(2) Mixing

The curcumin nanoparticle, starch sodium octenyl succinate and the Tribute Citrus concentrate were mixed by stirring to obtain a first mixture.

(3) Homogenization

The mixture obtained in step (2) was homogenized by a high-pressure homogenizer to obtain a first homogenized product.

(4) Compounding

The first homogenized product obtained in step (3) was compounded with the CMC-Na, xanthan gum, citric acid and xylitol to produce a second mixture.

(5) Secondary homogenization

The second mixture obtained in step (2) was homogenized by the high-pressure homogenizer to obtain a second homogenized product.

(6) Degassing

The second homogenized product was heated in a water bath at 80° C. for 15 min, and then degassed to obtain a degassed product.

(7) Bottling and sterilization

The degassed product was bottled and sterilized to produce the curcumin beverage.

To obtain the optimal curcumin beverage, the preparation of the curcumin beverage was optimized by experimental example 2.

Experimental Example 2 Optimization of Preparation of Curcumin Beverage Determination of Homogenization Pressure The homogenization was performed twice. With regard to the experimental group 1, the two homogenization steps were performed sequentially at 25 MPa and 5 MPa; while for the experimental group 2, the two homogenization steps were performed sequentially at 5 MPa and 25 MPa. The non-homogenized curcumin beverage was used as control (experimental group 3). The effect of homogenization on the particle size was presented in Table 10.

TABLE 10

Effect of homogenization on particle size

| Group | Pressure of primary homogenization | Pressure of secondary homogenization | $D_{50}$ (μm) |
|---|---|---|---|
| 1 | 25 | 5 | 16.795 |
| 2 | 5 | 25 | 100.656 |
| 3 | 0 | 0 | 417.56 |

Figure 8:
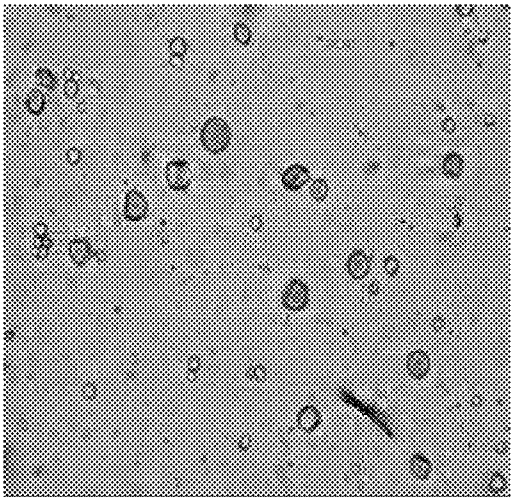
FIG. 8 is a 100× micrograph of the curcumin nanoparticle treated under conditions of experimental group 1 according to Experimental Example 2 of the disclosure.
Figure 9:
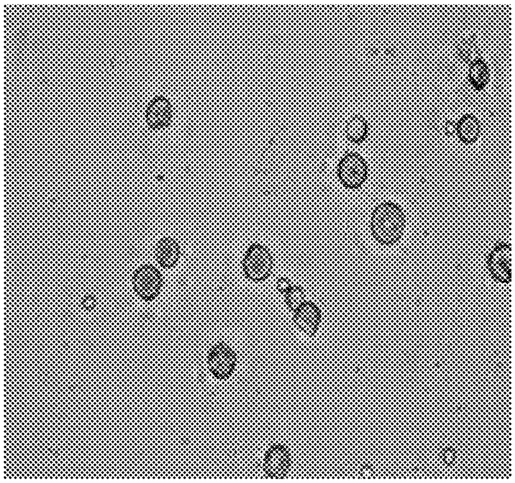
FIG. 9 is a 100× micrograph of the curcumin nanoparticle treated under conditions of experimental group 2 according to Experimental Example 2 of the disclosure.
Figure 10:
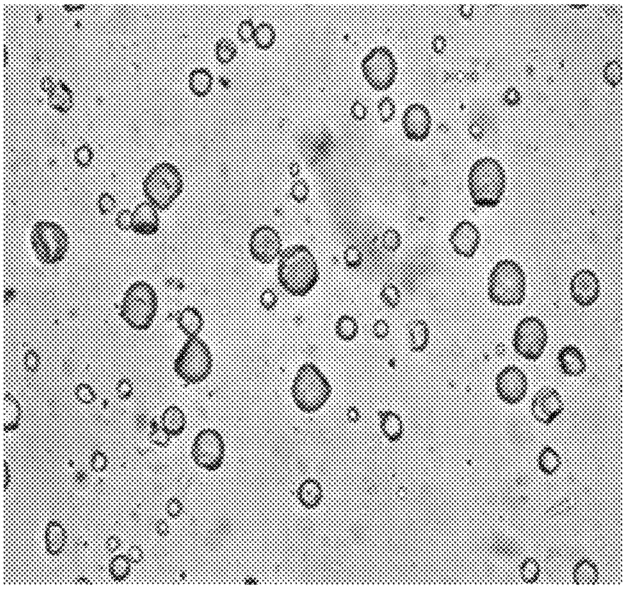
FIG. 10 is a 100× micrograph of the curcumin nanoparticle treated under conditions of experimental group 3 according to Experimental Example 2 of the disclosure.

From the perspective of particle size, the experimental group 1 was superior to the experimental group 2, and the experimental group 2 was better than the group 1. Referring to FIGS. 8-10, it can be seen that when the primary and secondary homogenization pressures were 25 MPa and 5 MPa, respectively, the large particles were crushed more completely into small particles, facilitating improving the storage stability of drinks; and by comparison, when the primary and secondary homogenization pressures were 5 MPa and 25 MPa, the large particles can be crushed, but the effect was inferior to that of the experimental group 1. The $D_{50}$ of the experimental groups 1-2 was superior to that of the experimental group 3 which did not undergo homogenization. Therefore, the homogenization conditions of the experimental group 1 were employed.

Determination of Sterilization Conditions

The curcumin beverage was a low-acid food (pH 6), so it can be sterilized at high temperature and high pressure (121° C. for 10 min). Moreover, it can also be acidified with citric acid to pH 4.6 and then pasteurized at 80° C. for 20 min; or filtered with a 0.22 μm organic filter for cold sterilization. The unsterilized beverage was used as control. The scavenging capacity toward DPPH free radical was used as an index to evaluate the sterilization effect, where the ascorbic acid (Vc) was used as positive control. The results were shown in Table 11.

Analysis of Antioxidant Property

The beverage samples were prepared as follows. Freeze-dried curcumin nanoparticle powder and starch sodium octenyl succinate were used as raw materials, and xanthan gum and CMC-Na were used as stabilizers. A 100 mg/mL curcumin beverage was prepared according to the above process, and then diluted with distilled water to 20 μg/mL, 40 μg/mL, 60 μg/mL, 80 μg/mL and 100 μg/mL.

2 mg, 4 mg, 6 mg, 8 mg and 10 mg of Vc were diluted with distilled water to 100 mL, respectively, that was, the final concentrations of the Vc were 20 μg/mL, 40 μg/mL, 60 μg/mL, 80 μg/mL and 100 μg/mL, respectively.

TABLE 11

Conditions for sterilization

| Sample | Conditions for sterilization | DPPH• scavenging activity of sample $IC_{50}$ ($\mu g \cdot mL^{-1}$) | DPPH• scavenging activity of $V_C$ $IC_{50}$ ($\mu g \cdot mL^{-1}$) | Total colony count (CFU/mL) |
|---|---|---|---|---|
| 1 | 121° C./10 min | 55.71 ± 3.89 | 15.81 ± 5.04 | 6 |
| 2 | 80° C./20 min | 193.3 ± 3.7 | 22.74 ± 8.59 | 5 |
| 3 | 0.22 μm organic filter | 67.19 ± 4.94 | 13.63 ± 4.52 | 38 |
| 4 | Unsterilized | 41.95 ± 4.79 | 11.19 ± 5.32 | 198 |

It can be seen from Table 11 that in terms of $IC_{50}$ value, the four sample groups were sequentially 2, 3, 4 and 1 from highest to lowest, and the four Vc positive control groups were sequentially 2, 1, 3 and 4 from highest to lowest. A lower $IC_{50}$ value indicated higher DPPH• scavenging rate, indicating a better antioxidant property. Therefore, the sample 1 has the highest antioxidant property. Compared to the unsterilized sample, the three sterilized samples all exhibited higher $IC_{50}$. With regard to the sample 2, since it was acidified to pH 4.6 and the acid group anion had an inhibitory effect on the superoxide anion, it had the highest $IC_{50}$ value, which indicated that the sample 2 had the lowest scavenging activity toward DPPH• and the poorest antioxidant property. The total colony counts of the samples 1-3 met the related standards mentioned in GB 7101-2015 "National Food Safety Standards (drinks)", while the total colony count of the unsterilized sample did not meet the national standards. In conclusion, the sterilization condition of 121° C./10 min was preferred.

Example 3

Provided herein was a curcumin beverage, consisting of:
15% by weight of Tribute Citrus concentrate;
0.15% by weight of xanthan gum;
0.8% by weight of the curcumin nanoparticle;
0.4% by weight of starch sodium octenyl succinate;
0.15% by weight of CMC-Na;
0.1% by weight of citric acid;
10% by weight of xylitol; and
water.

Specifically, the addition of 0.8% by weight of the curcumin nanoparticle made the curcumin beverage have activities of improving the activity of superoxide dismutase (SOD) and reducing the level of malondialdehyde (MDA), showing anti-aging and antioxidation effects.

The curcumin beverage was made according to the above process.

Experimental examples 3-6 were conducted to investigate the influence of the additive amount of CMC-Na, xanthan gum, nanocurcumin and starch sodium octenyl succinate on the quality of the curcumin beverage.

Criteria for evaluating the quality of the curcumin beverage were established.

Criteria for evaluating the quality of the curcumin beverage

Criteria of Sensory Evaluation

The sensory indexes of the curcumin beverage were evaluated by 8 members.

TABLE 12

Criteria of sensory score

| Item | Index | Score |
|---|---|---|
| Color and luster (Full mark 20) | Even color, orange | 11-20 |
| Odor | Relatively dark color | 0-10 |
| (Full mark 30) | Curcumin odor and orange odor, no peculiar smell | 15-30 |
| Taste | Light curcumin odor, no peculiar odor | 0-15 |
| (Full mark 30) | Pure taste, moderate sour and sweet taste, no peculiar taste | 20-30 |
| State of tissue | Relatively pure taste, slightly sour or sweet | 10-20 |
| (Full mark 20) | | |
| | Unpalatable taste, sour or sweet | 0-10 |
| | Even turbidity in juice, stable | 10-20 |
| | Precipitates in juice, uneven | 0-10 |

Stability of Absorbance

A certain amount of the curcumin nanoparticle was diluted 20 times with water, mixed uniformly and centrifuged at 4,000 r/min for 15 min. The absorbance ($A_0$) of the sample before the centrifugation and the absorbance (A) of the sample after the centrifugation were measured at the maximum absorption wavelength, and the stability of absorbance was represented by $A/A_0$.

Precipitation Rate after Centrifugation

The weight of the centrifuge tube and the total weight of the sample and the centrifuge tube were measured, and then the sample was centrifuged at 4,000 r/min for 15 min. The supernatant was discarded and the total weight of the centrifuge tube and the precipitate was accurately measured.

The precipitation rate was calculated as follows: precipitation rate=precipitate weight/sample weight×100%.

Measurement of DPPH• scavenging activity (1) Sample preparation

The beverage samples were prepared as follows. Freeze-dried curcumin nanoparticle powder and starch sodium octenyl succinate were used as raw materials, and xanthan gum and CMC-Na were used as stabilizers. A 100 mg/mL curcumin beverage was prepared according to the above process, and then diluted with distilled water to 20 μg/mL, 40 μg/mL, 60 μg/mL, 80 μg/mL and 100 μg/mL.

2 mg, 4 mg, 6 mg, 8 mg and 10 mg of Vc were diluted with distilled water to 100 mL, respectively, that was, the final concentrations of the Vc were 20 μg/mL, 40 μg/mL, 60 μg/mL, 80 μg/mL and 100 μg/mL, respectively.

(2) Measurement of DPPH• scavenging activity 100 μL of a solution of DPPH in ethanol (0.2 mmol/L) was added to a 96-well plate, to which 100 μL of different concentrations of the curcumin beverages was added and mixed uniformly. The reaction mixture was reacted in dark for 30 min, and then measured at 517 nm for the absorbance ($A_1$), where a well containing the sample and 100 μL of absolute ethanol was used as control; a well containing 100 μL of distilled water and 100 μL of the DPPH solution was used as blank group; and Vc was used as positive control.

The scavenging rate was calculated as follows: scavenging rate %=[1−($A_1$−$A_2$)/$A_0$]×100%, where:

$A_0$: absorbance of the mixture of 100 μL of distilled water and 100 μL of the solution of DPPH in ethanol;

$A_1$: absorbance of the mixture of 100 μL of sample and 100 μL of the solution of DPPH in ethanol;

$A_2$: absorbance of the mixture of 100 μL of sample and 100 μL of absolute ethanol.

Measurement of $ABTS^{+}$• scavenging activity (1) Sample preparation

The beverage samples were prepared as follows. Freeze-dried curcumin nanoparticle powder and starch sodium octenyl succinate were used as raw materials, and xanthan gum and CMC-Na were used as stabilizers. A 100 mg/mL curcumin beverage was prepared according to the above process, and then diluted with distilled water to 20 μg/mL, 40 μg/mL, 60 μg/mL, 80 μg/mL and 100 m/mL.

2 mg, 4 mg, 6 mg, 8 mg and 10 mg of Vc were diluted with distilled water to 100 mL, respectively, that was, the final concentrations of the Vc were 20 μg/mL, 40 μg/mL, 60 μg/mL, 80 μg/mL and 100 m/mL, respectively.

(2) Measurement of $ABTS^{+}$• scavenging activity 5 mL of a $K_2S_2O_8$ solution (2.6 mmol/L) and 10 mL of an $ABTS^{+}$• solution (7.4 mmol/L) were mixed uniformly and reacted in dark for 12 h. The $ABTS^{+}$• solution was diluted with phosphate buffer solution (pH=6.6) to an absorbance of 0.70±0.02 to produce a working solution. 40 μL of different concentrations of curcumin beverages was added in a 96-well plate, to which 160 μL of the $ABTS^{+}$• working solution was added. The reaction mixture was mixed uniformly, reacted in dark for 6 min and measured at 734 nm for the absorbance $A_1$, where a well containing the sample and 160 μL of absolute ethanol was used as control; a well containing 40 μL of distilled water and 160 μL of the $ABTS^{+}$• solution was used as blank group; and Vc was used as positive control.

The scavenging rate was calculated as follows: scavenging rate %=[1−($A_1$−$A_2$)/$A_0$]×100%, where:

$A_0$: absorbance of the mixture of 40 μL of distilled water and 160 μL of the $ABTS^{+}$• solution;

$A_1$: absorbance of the mixture of 40 μL of the sample and 160 μL of the $ABTS^{+}$• solution;

$A_2$: absorbance of the mixture of 40 μL of the sample liquid and 160 μL of absolute ethyl alcohol.

Comprehensive Scoring

The formula of the curcumin beverage was determined by comprehensive scoring. The sensory score, absorbance stability, precipitation rate, capacity of DPPH• scavenging activity, and $ABTS^{+}$• scavenging activity were used as indexes for assessment, where the total score=sensory score×its weight+absorbance stability score×its weight+score of precipitation rate×its weight+score of DPPH• scavenging rate×its weight+score of $ABTS^{+}$• scavenging rate×its weight.

The level distribution, ranking score, and weight distribution were shown respectively in Table 13, Table 14, and Table 15.

TABLE 13

| | Level distribution | | | |
|---|---|---|---|---|
| | Index | | | |
| Level | Coefficient of absorbency stability | Precipitation rate after centrifugation | Rate of DPPH•radical clearance (%) | Rate of $ABTS^{+}$•radical clearance (%) |
| 1 | ≥0.4 | ≤0.4 | ≥80.00 | ≥80.00 |
| 2 | 0.3~0.4 | 0.4~0.6 | 80.00~60.00 | 80.00~60.00 |
| 3 | 0.3~0.2 | 0.6~0.8 | 60.00:40.00 | 60.00~40.00 |
| 4 | ≤0.3 | ≥0.8 | ≤40.00 | ≤40.00 |

TABLE 14

| | Ranking score | | | |
|---|---|---|---|---|
| Rank | 1 | 2 | 3 | 4 |
| Score | 100 | 80 | 50 | 30 |

TABLE 15

| Weight distribution | |
|---|---|
| Index | Weight |
| Sensory score | 0.2 |
| Stability of absorbance | 0.2 |
| Precipitation rate after centrifugation | 0.2 |
| DPPH• scavenging rate | 0.2 |
| $ABTS^{+}$• scavenging rate | 0.2 |

Experimental Example 3 Influence of the Addition Amount of CMC-Na on the Quality of the Curcumin Beverage A series of curcumin beverages containing 0.4% by weight of the curcumin nanoparticle, 0.4% by weight of starch sodium octenyl succinate, 0.1% by weight of xanthan gum, 10% by weight of xylitol, 0.1% by weight of citric acid and CMC-Na were prepared according the above process, where the addition amount of CMC-Na in the beverages was 0.05%, 0.1%, 0.15%, 0.2% and 0.25%, respectively. The sensory score, absorbance stability, precipitation rate after centrifugation, DPPH• scavenging rate and $ABTS^{+}$• scavenging rate were used as evaluation indexes to determine the optimal addition amount of CMC-Na. The results were shown in Table 16.

TABLE 16

Influence of the additive amount of CMC-Na on the quality of the curcumin beverage

| Additive amount of CMC-Na (%) | Sensory score | Coefficient of absorbance stability | Precipitation rate after centrifugation | DPPH · scavenging rate (%) | | ABTS$^+$ · scavenging rate (%) | | Comprehensive score |
|---|---|---|---|---|---|---|---|---|
| | | | | Sample | Vc | Sample | Vc | |
| 0.05 | 80 | 0.256 ± 0.005 | 0.379 ± 0.010 | 63.23 | 92.51 | 44.30 | 90.38 | 68.0 |
| 0.10 | 90 | 0.456 ± 0.011 | 0.357 ± 0.010 | 63.11 | 92.51 | 41.29 | 90.38 | 84.0 |
| 0.15 | 78 | 0.411 ± 0.016 | 0.384 ± 0.010 | 63.35 | 92.51 | 41.96 | 90.38 | 81.6 |
| 0.20 | 75 | 0.391 ± 0.030 | 0.393 ± 0.010 | 63.87 | 92.51 | 42.88 | 90.38 | 77.0 |
| 0.25 | 75 | 0.389 ± 0.004 | 0.396 ± 0.020 | 63.26 | 92.51 | 42.70 | 90.38 | 77.0 |

Figure 11:
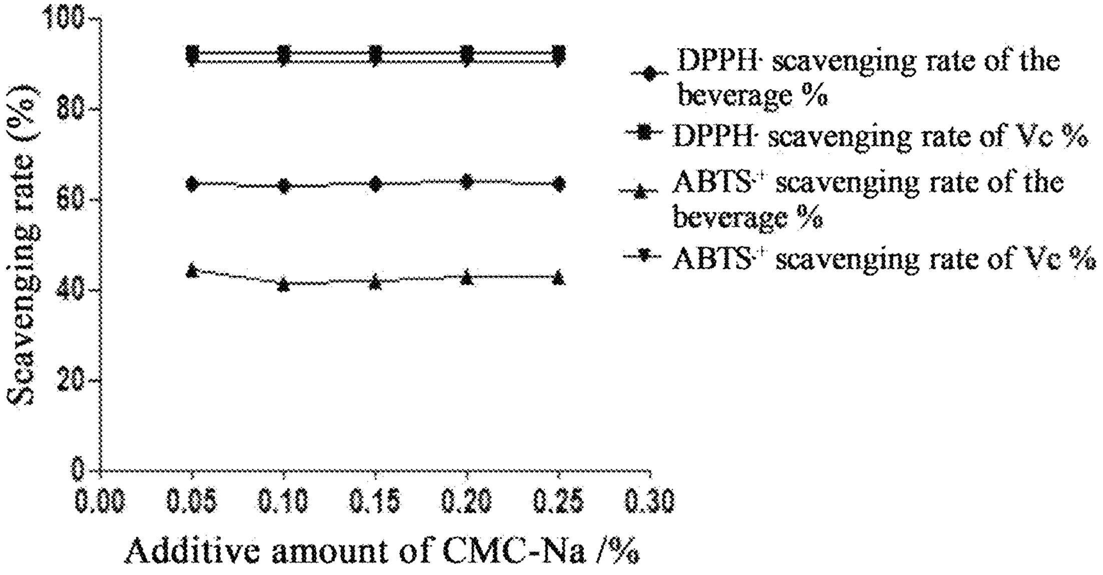
FIG. 11 shows the influence of the addition amount of CMC-Na on the free radical scavenging rate according to Experimental Example 3 of the disclosure.
Figure 12:
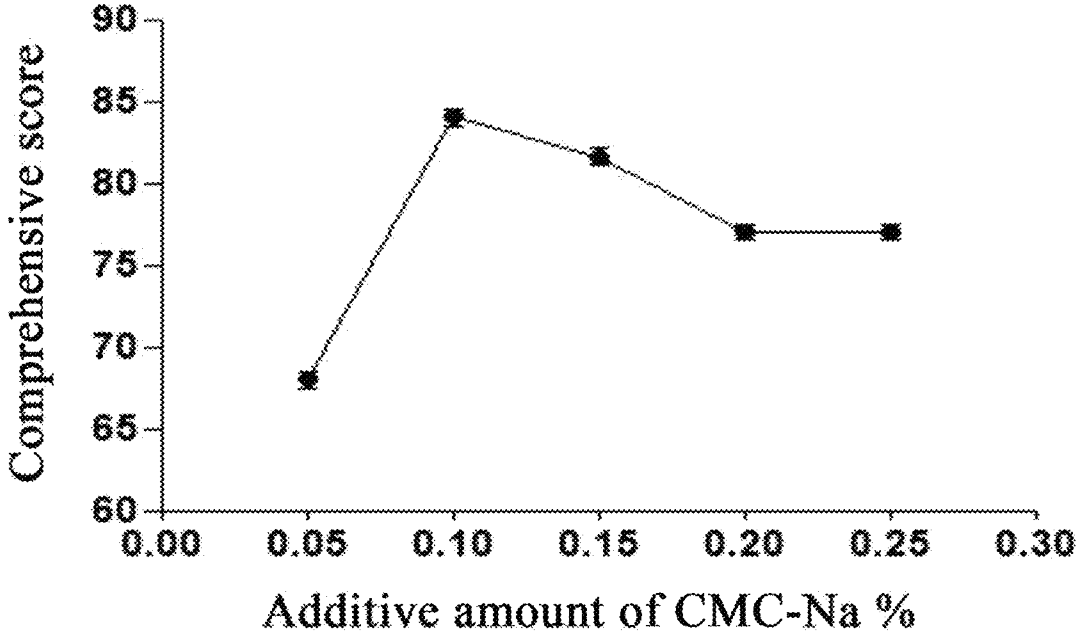
FIG. 12 shows the influence of the addition amount of CMC-Na on the curcumin beverage according to Experimental Example 3 of the disclosure.

It can be seen from Table 16 that the sensory score increased first and then decreased along with the increase of the additive amount of CMC-Na, and the sample with 0.1% by weight of CMC-Na had the highest sensory score. It was because with 0.1% CMC-Na, the drink did not experience precipitation or layering, and had the best taste. With the increase of the addition amount of CMC-Na, the taste of drink gradually became bad. When 0.1% CMC-Na was added, the system was in a stable state, exhibiting the highest coefficient of absorbance stability and lowest precipitation rate after centrifugation. With the increase of CMC-Na, the stable state was broken, leading to a decline in the coefficient of absorbance stability and an increase in the precipitation rate. It can be observed from FIG. 11 that the addition amount of CMC-Na had little influence on the DPPH• scavenging rate and the ABTS$^+$• scavenging rate. It can be seen from Table 16, FIG. 11 and FIG. 12 that the drink with 0.1% CMC-Na had the highest comprehensive score, indicating that the optimal addition amount of CMC-Na was 0.1%.

Experimental Example 4 Influence of the Additive Amount of Xanthan Gum on the Quality of the Curcumin Beverage A series of curcumin beverages containing 0.4% by weight of the curcumin nanoparticle, 0.4% by weight of starch sodium octenyl succinate, 0.1% by weight of CMC-Na, 10% by weight of xylitol, 0.1% by weight of citric acid and xanthan gum were prepared according the above process, where the addition amount of xanthan gum in the beverages was 0.05%, 0.1%, 0.15%, 0.2% and 0.25%, respectively. The sensory score, absorbance stability, precipitation rate after centrifugation, DPPH• scavenging rate and ABTS$^+$• scavenging rate were used as evaluation indexes to determine the optimal addition amount of xanthan gum. The results were shown in Table 17.

TABLE 17

Influence of the additive amount of xanthan gum on the quality of the curcumin beverage

| Additive amount of xanthan gum/% | Sensory score | Coefficient of absorbance stability | Precipitation rate after centrifugation | DPPH · scavenging rate (%) | | ABTS$^+$ · scavenging rate (%) | | Comprehensive score |
|---|---|---|---|---|---|---|---|---|
| | | | | Sample | Vc | Sample | Vc | |
| 0.05 | 80 | 0.351 ± 0.010 | 0.410 ± 0.010 | 45.65 | 92.51 | 37.17 | 90.38 | 64.6 |
| 0.10 | 83 | 0.385 ± 0.010 | 0.360 ± 0.010 | 45.06 | 92.51 | 37.76 | 90.38 | 68.6 |
| 0.15 | 90 | 0.555 ± 0.010 | 0.331 ± 0.010 | 45.27 | 92.51 | 36.70 | 90.38 | 74.0 |
| 0.20 | 83 | 0.542 ± 0.020 | 0.348 ± 0.010 | 45.74 | 92.51 | 37.54 | 90.38 | 72.6 |
| 0.25 | 80 | 0.509 ± 0.010 | 0.371 ± 0.010 | 45.27 | 92.51 | 37.85 | 90.38 | 72.0 |

Figure 13:
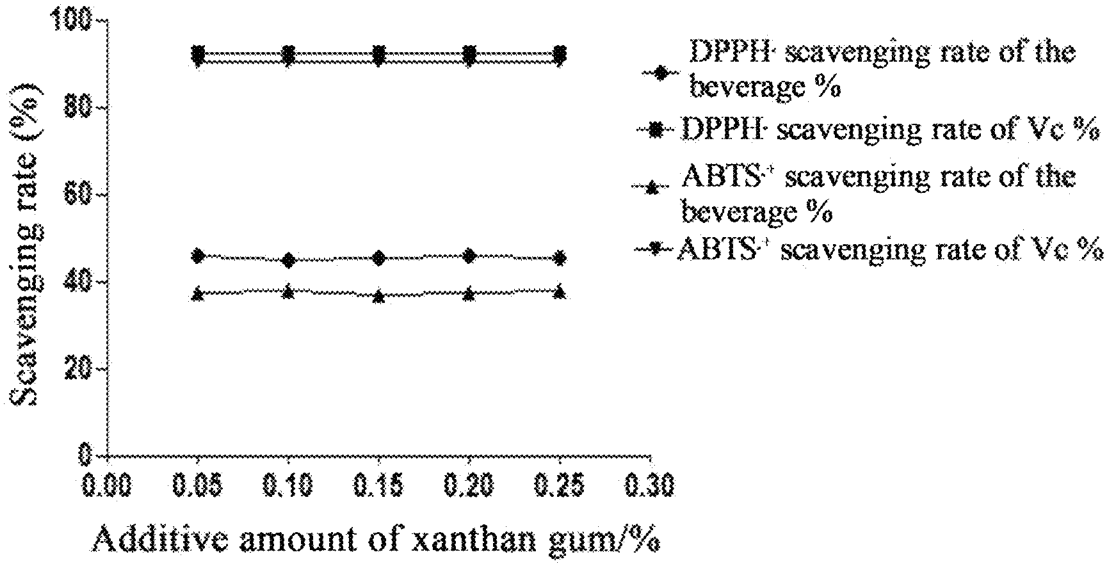
FIG. 13 shows the influence of the addition amount of xanthan gum on the free radical scavenging rate according to Experimental Example 4 of the disclosure.
Figure 14:
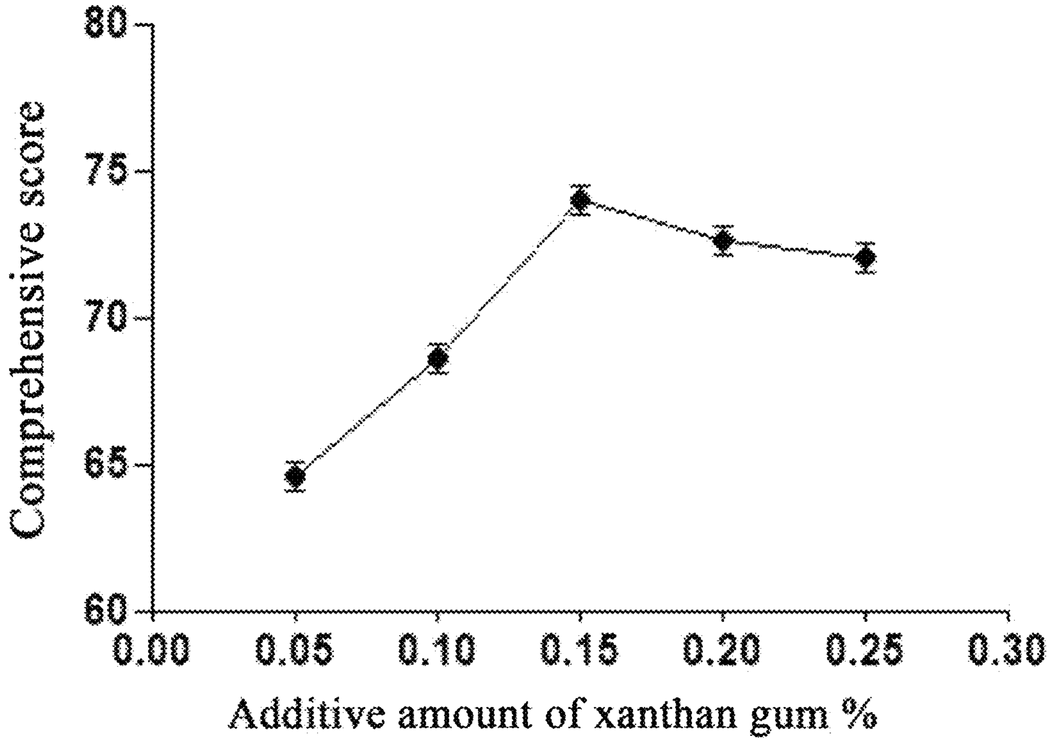
FIG. 14 shows the influence of the addition amount of xanthan gum on the curcumin beverage according to Experimental Example 4 of the disclosure.

It can be seen from Table 17 that the sensory score increased first and then decreased along with the increase of the additive amount of xanthan gum, and the sample with 0.15% by weight of xanthan gum had the highest sensory score. It was because with 0.15% xanthan gum, the drink did not experience precipitation or layering, and had the best taste. With the increase of the addition amount of xanthan gum, the drink became more viscous, affecting the taste. When 0.15% xanthan gum was added, the system was in a stable state, exhibiting the highest coefficient of absorbance stability and lowest precipitation rate after centrifugation. With the increase of xanthan gum, the stable state was broken, leading to a decline in the coefficient of absorbance stability and an increase in the precipitation rate. It can be observed from FIG. 13 that the addition amount of xanthan gum had little influence on the DPPH• scavenging rate and the $ABTS^{+}$• scavenging rate. It can be seen from Table 17, FIG. 13 and FIG. 14 that the drink with 0.15% xanthan gum had the highest comprehensive score, indicating that the optimal addition amount of xanthan gum was 0.15%.

Experimental Example 5 Influence of the Additive Amount of Starch Sodium Octenyl Succinate on the Quality of the Curcumin Beverage A series of curcumin beverages containing 0.4% by weight of the curcumin nanoparticle, 0.1% by weight of xanthan gum, 0.1% by weight of CMC-Na, 10% by weight of xylitol, 0.1% by weight of citric acid and starch sodium octenyl succinate were prepared according the above process, where the addition amount of starch sodium octenyl succinate in the beverages was 0.2%, 0.4%, 0.6%, 0.8% and 1.0%, respectively. The sensory score, absorbance stability, precipitation rate after centrifugation, DPPH• scavenging rate and $ABTS^{+}$• scavenging rate were used as evaluation indexes to determine the optimal addition amount of starch sodium octenyl succinate. The results were shown in Table 18.

Figure 15:
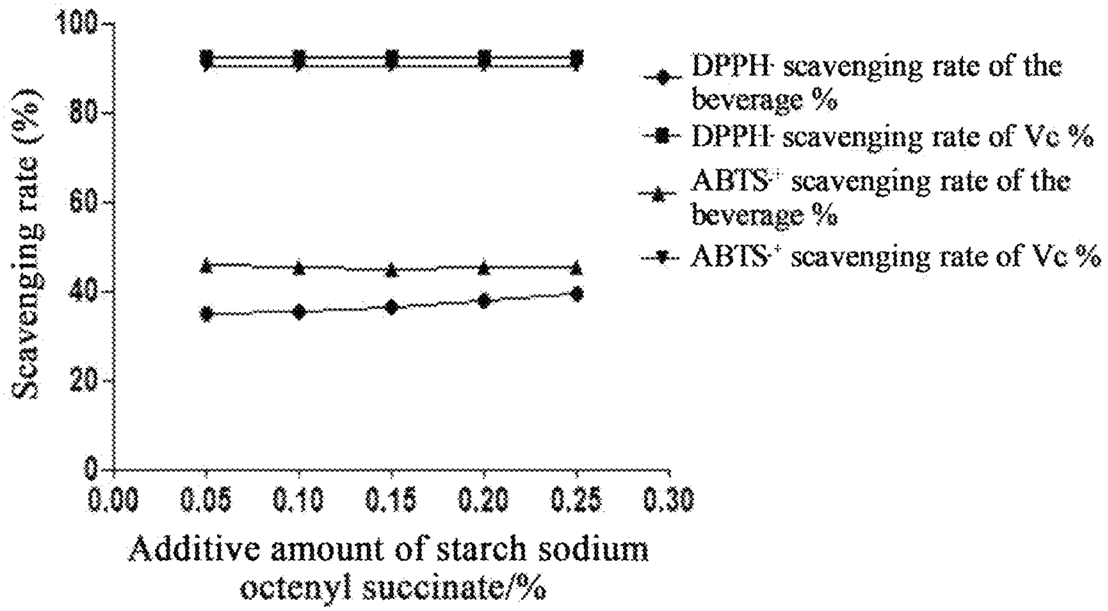
FIG. 15 shows the influence of the addition amount of starch sodium octenyl succinate on the free radical scavenging rate according to Experimental Example 5 of the disclosure.
Figure 16:
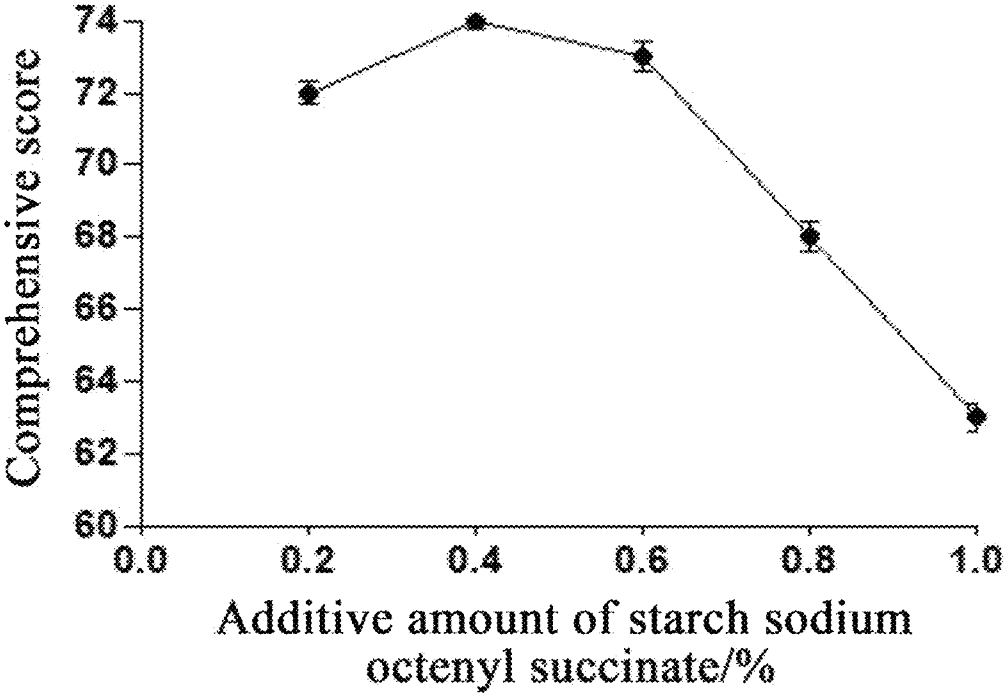
FIG. 16 shows the influence of the addition amount of starch sodium octenyl succinate on the curcumin beverage according to Experimental Example 5 of the disclosure.

It can be seen from Table 18 that the sensory score increased first and then decreased along with the increase of the additive amount of starch sodium octenyl succinate, and the sample with 0.4% by weight of starch sodium octenyl succinate had the highest sensory score. It was because with 0.4% starch sodium octenyl succinate, the drink exhibited the highest level of odors of starch sodium octenyl succinate and curcumin. With the increase of the addition amount of starch sodium octenyl succinate, the odor of starch sodium octenyl succinate was too strong, masking the odor of curcumin and deteriorating the taste. With the increase of starch sodium octenyl succinate, the coefficient of absorbance stability experienced a decline and the precipitation rate experienced an increase. It can be observed from FIG. 15 that the addition amount of starch sodium octenyl succinate had little influence on the $ABTS^{+}$• scavenging rate, but with the increase of the starch sodium octenyl succinate, the DPPH• scavenging rate was slightly improved. It can be seen from Table 18, FIG. 15 and FIG. 16 that the drink with 0.4% starch sodium octenyl succinate had the highest comprehensive score, indicating that the optimal addition amount of starch sodium octenyl succinate was 0.4%.

Experimental Example 6 Influence of the Additive Amount of Curcumin Nanoparticle on the Quality of the Curcumin Beverage A series of curcumin beverages containing 0.4% by weight of the starch sodium octenyl succinate, 0.1% by weight of xanthan gum, 0.1% by weight of CMC-Na, 10% by weight of xylitol, 0.1% by weight of citric acid and starch sodium octenyl succinate were prepared according the above process, where the addition amount of the curcumin nanoparticle in the beverages was 0.2%, 0.4%, 0.6%, 0.8% and 1.0%, respectively. The sensory score, absorbance stability, precipitation rate after centrifugation, DPPH• scavenging rate and $ABTS^{+}$• scavenging rate were used as evaluation indexes to determine the optimal addition amount of curcumin nanoparticle. The results were shown in Table 19.

TABLE 18

Influence of the additive amount of starch sodium octenyl succinate on the quality of the curcumin beverage

| Addictive amount of starch sodium octenyl succinate/% | Sensory score | Coefficient of absorbance stability | Precipitation rate after centrifugation | DPPH · scavenging rate (%) | | $ABTS^{+}$ · scavenging rate (%) | | Comprehensive score |
|---|---|---|---|---|---|---|---|---|
| | | | | Sample | Vc | Sample | Vc | |
| 0.2 | 80 | 0.585 ± 0.01 | 0.340 ± 0.01 | 35.02 | 92.51 | 45.60 | 90.38 | 72 |
| 0.4 | 90 | 0.503 ± 0.01 | 0.342 ± 0.01 | 35.19 | 92.51 | 45.13 | 90.38 | 74 |
| 0.6 | 85 | 0.469 ± 0.01 | 0.363 ± 0.01 | 36.51 | 92.51 | 45.07 | 90.38 | 73 |
| 0.8 | 80 | 0.415 ± 0.01 | 0.404 ± 0.01 | 37.82 | 92.51 | 45.10 | 90.38 | 68 |
| 1.0 | 75 | 0.368 ± 0.01 | 0.421 ± 0.01 | 39.09 | 92.51 | 45.27 | 90.38 | 63 |

TABLE 19

Influence of the additive amount of curcumin nanoparticle on the quality of the curcumin beverage

| Freeze-dried curcumin nanoparticle powder | Sensory score | Coefficient of absorbency stability | Precipitation rate after centrifugation | Rate of DPPH · radical clearance (%) | | Rate of $ABTS^+$ · radical clearance (%) | | Comprehensive score |
|---|---|---|---|---|---|---|---|---|
| | | | | Sample | Vc | Sample | Vc | |
| 0.2 | 80 | 0.505 ± 0.01 | 0.393 ± 0.01 | 53.43 | 91.72 | 40.46 | 88.12 | 76.0 |
| 0.4 | 84 | 0.447 ± 0.01 | 0.429 ± 0.01 | 63.18 | 92.51 | 43.74 | 90.38 | 78.8 |
| 0.6 | 90 | 0.398 ± 0.01 | 0.446 ± 0.01 | 80.63 | 93.15 | 50.04 | 92.44 | 85.0 |
| 0.8 | 95 | 0.261 ± 0.01 | 0.486 ± 0.02 | 80.93 | 93.62 | 60.15 | 93.69 | 87.0 |
| 1.0 | 85 | 0.225 ± 0.01 | 0.547 ± 0.02 | 81.04 | 93.67 | 61.11 | 94.53 | 79.0 |

Figure 17:
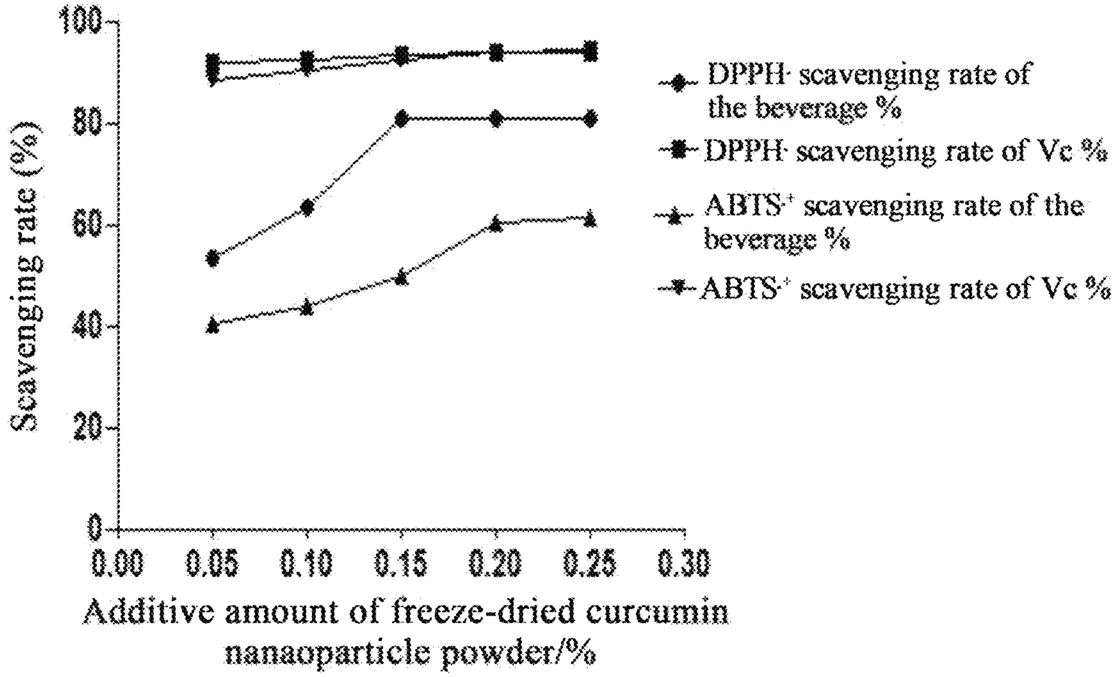
FIG. 17 shows the influence of the addition amount of freeze-dried curcumin powder on the free radical scavenging rate according to Experimental Example 6 of the disclosure.
Figure 18:
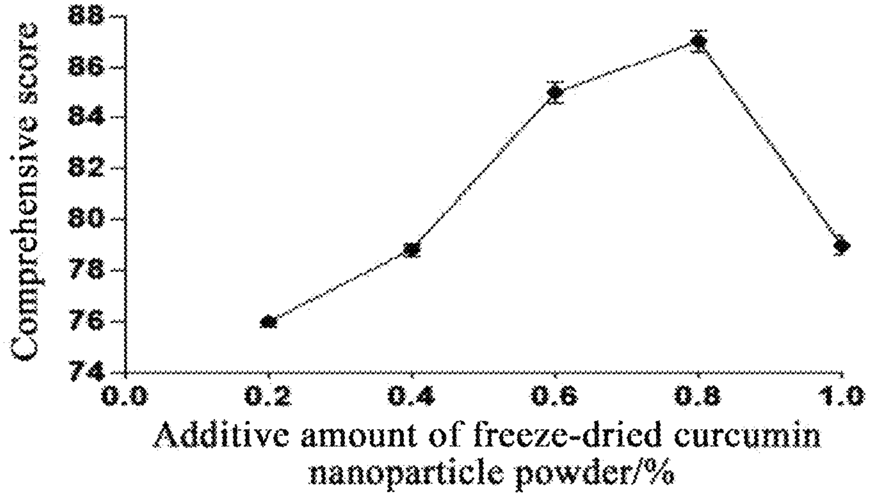
FIG. 18 shows the influence of the addition amount of freeze-dried curcumin powder on the curcumin beverage according to Experimental Example 6 of the disclosure.

It can be seen from Table 19 that the sensory score increased first and then decreased along with the increase of the additive amount of the curcumin nanoparticle, and the sample with 0.8% by weight of the curcumin nanoparticle had the highest sensory score. It was because with 0.8% curcumin nanoparticle, the drink showed strong curcumin odor, and with the increase of the addition amount of the curcumin nanoparticle, the odor of the curcumin nanoparticle was too strong, affecting the sensory evaluation. With the increase of the curcumin nanoparticle, the coefficient of absorbance stability experienced a decline and the precipitation rate experienced an increase. It can be observed from FIG. 17 that the addition amount of the curcumin nanoparticle was positively associate with the $ABTS^{+}$• scavenging rate and the DPPH• scavenging rate. It can be seen from Table 19, FIG. 17 and FIG. 18 that the drink with 0.8% curcumin nanoparticle had the highest comprehensive score, indicating that the optimal addition amount of the curcumin nanoparticle was 0.8%.

To determine the optimal combination of the additive amounts of CMC-Na, xanthan gum, the curcumin nanoparticle and starch sodium octenyl succinate, an orthogonal experiment was performed as follows.

Orthogonal Experiment

The formula of the curcumin beverage was optimized by $L_9(3^4)$ orthogonal experiment in which addition amounts of CMC-Na (A), xanthan gum (B), nanocurcumin (C) and starch sodium octenyl succinate (D) were used as experimental factors, and sensory score, absorbance stability, precipitation rate after centrifugation, DPPH• scavenging rate and $ABTS^{+}$• scavenging rate were used as evaluation indexes. The orthogonal experiment was designed as shown in Tables 20-21.

TABLE 20

$L_9(3^4)$ orthogonal table

| Level | Factor | | | |
|---|---|---|---|---|
| | A Additive amount of CMC-Na (%) | B Additive amount of xanthan gum (%) | C Additive amount of freeze-dried curcumin powder (%) | D Addictive amount of starch sodium octenyl succinate (%) |
| 1 | 0.05 | 0.10 | 0.2 | 0.6 |
| 2 | 0.10 | 0.15 | 0.4 | 0.8 |
| 3 | 0.15 | 0.20 | 0.6 | 1.0 |

TABLE 21

Value of evaluation indices of experimental groups

| Test number | Sensory score | Coefficient of absorbance stability | Precipitation rate after centrifugation | DPPH · scavenging rate (%) | | $ABTS^+$ · scavenging rate (%) | | Comprehensive score |
|---|---|---|---|---|---|---|---|---|
| | | | | Sample | Vc | Sample | Vc | |
| 1 | 80 | 0.493 ± 0.2 | 0.435 ± 0.2 | 79.26 | 93.44 | 79.80 | 92.88 | 84.0 |
| 2 | 88 | 0.470 ± 0.1 | 0.374 ± 0.2 | 84.41 | 94.65 | 82.41 | 95.10 | 97.6 |
| 3 | 82 | 0.479 ± 0.2 | 0.444 ± 0.2 | 78.89 | 95.72 | 78.70 | 96.13 | 80.4 |
| 4 | 75 | 0.480 ± 0.2 | 0.370 ± 0.1 | 79.14 | 95.72 | 77.17 | 96.13 | 87.0 |
| 5 | 75 | 0.382 ± 0.2 | 0.371 ± 0.3 | 75.44 | 93.44 | 79.13 | 92.88 | 83.0 |
| 6 | 79 | 0.573 ± 0.2 | 0.363 ± 0.3 | 78.05 | 94.65 | 77.33 | 95.10 | 87.8 |
| 7 | 83 | 0.328 ± 0.3 | 0.361 ± 0.1 | 74.10 | 94.65 | 80.26 | 95.10 | 88.6 |
| 8 | 82 | 0.524 ± 0.1 | 0.403 ± 0.1 | 75.50 | 95.72 | 77.06 | 96.13 | 84.4 |
| 9 | 72 | 0.502 ± 0.1 | 0.371 ± 0.1 | 77.80 | 93.44 | 78.70 | 92.88 | 86.4 |

Results and Analysis

TABLE 22

Results of $L_9(3^4)$ orthogonal experiment

| Test number | A Additive amount of CMC-Na (%) | B Additive amount of xanthan gum (%) | C Additive amount of starch sodium octenyl succinate (%) | D Additive amount of the freeze-dried curcumin nano-particle powder | Com-pre-hensive score (%) |
|---|---|---|---|---|---|
| 1 | 1(0.05) | 1(0.10) | 1(0.2) | 1(0.6) | 84.0 |
| 2 | 1(0.05) | 2(0.15) | 2(0.4) | 2(0.8) | 97.6 |
| 3 | 1(0.05) | 3(0.20) | 3(0.6) | 3(1.0) | 80.4 |
| 4 | 2(0.10) | 1(0.10) | 2(0.4) | 3(1.0) | 87.0 |
| 5 | 2(0.10) | 2(0.15) | 3(0.6) | 1(0.6) | 83.0 |
| 6 | 2(0.10) | 3(0.20) | 1(0.2) | 2(0.8) | 87.8 |
| 7 | 3(0.15) | 1(0.10) | 3(0.6) | 2(0.8) | 88.6 |
| 8 | 3(0.15) | 2(0.15) | 1(0.2) | 3(1.0) | 84.4 |
| 9 | 3(0.15) | 3(0.20) | 2(0.4) | 1(0.6) | 86.4 |
| $K_1$ | 87.333 | 86.533 | 85.400 | 84.467 | |
| $K_2$ | 95.933 | 88.333 | 90.333 | 91.333 | |
| $K_3$ | 96.467 | 84.867 | 84.000 | 83.933 | |
| R | 1.400 | 3.466 | 6.333 | 7.400 | |
| Optimal combination | $A_3B_2C_2D_2$ | | | | |
| Significance of factors | D>C>B>A | | | | |

It can be seen from the R values in Table 22 that in terms of the influence on the quality of the curcumin beverage, the four factors were sequentially D, C, B and A from the largest to lowest, that was, the addition amount of the freeze-dried curcumin nanoparticle powder was the primary influencing factor, followed by the amount of starch sodium octenyl succinate, the amount of xanthan gum and the amount of CMC-Na. It can be seen from K values that the optimal combination was $A_3B_2C_2D_2$, that was, the additive amounts of CMC-Na, xanthan gum, starch sodium octenyl succinate and curcumin nanoparticle were 0.15%, 0.15%, 0.4% and 0.8%, respectively.

The variance analysis of results of orthogonal experiment was shown in Table 23.

TABLE 23

Variance analysis of orthogonal experiment

| Factor | DEVSQ | Degree of freedom | F-ratio | F critical-value | Sig-nifi-cance |
|---|---|---|---|---|---|
| CMC-Na | 2.996 | 2 | 1.000 | 19.000 | |
| Xanthan gum | 18.036 | 2 | 6.020 | 19.000 | |
| Starch sodium octenyl succinate | 66.409 | 2 | 22.166 | 19.000 | * |
| Freeze-dried curcumin nanoparticle-powder | 102.196 | 2 | 34.111 | 19.000 | * |
| Error | 3.00 | 2 | | | |

It can be observed from Table 23 that the curcumin nanoparticle and starch sodium octenyl succinate can significantly influence the quality of the curcumin beverage, and the influence of the former was more significant than the latter. CMC-Na and xanthan gum were insignificant factors.

The following verification experiment was conducted to verify the reliability of the orthogonal experiment.

The optimal orthogonal group was $A_3B_2C_2D_2$. The verification experiment was repeated three times, and the results were shown in Table 24, from which it can be found that the comprehensive score of the curcumin drink was 98.64, verifying the reliability of the orthogonal experiment. Therefore, $A_3B_2C_2D_2$ was considered to be the optimal combination.

TABLE 24

Verification experiment

| Number | Sensory score | Coefficient of absorbance stability | Precipitation rate after centrifugation (%) | DPPH · scavenging rate (%) Sample | DPPH · scavenging rate (%) Vc | $ABTS^+$ · scavenging rate (%) Sample | $ABTS^+$ · scavenging rate (%) Vc | Comprehensive score |
|---|---|---|---|---|---|---|---|---|
| 1 | 93.00 | 0.525 | 0.385 | 83.33 | 94.59 | 85.11 | 95.34 | 98.60 |
| 2 | 93.50 | 0.513 | 0.375 | 82.49 | 94.59 | 85.89 | 95.34 | 98.60 |
| 3 | 93.50 | 0.518 | 0.377 | 83.14 | 95.59 | 84.99 | 95.34 | 98.70 |
| Mean | 93.33 ± 0.24 | 0.518 ± 0.005 | 0.378 ± 0.004 | 82.86 ± 0.36 | 94.5 ± 0.00 | 85.33 ± 0.40 | 95.34 ± 0.00 | 98.64 ± 0.05 |

In conclusion, the optimal formula of the curcumin beverage was listed as follows: 0.15% by weight of xanthan gum, 0.15% by weight of CMC-Na, 0.4% by weight of starch sodium octenyl succinate, 0.8% by weight of the freeze-dried curcumin nanoparticle powder, 0.1% by weight of citric acid and 10% by weight of xylitol. In this case, the product had the highest comprehensive score 98.64±0.05, where the sensory score was 93.33±0.24; the coefficient of absorbance stability was 0.518±0.005; and the precipitation rate after centrifugation was 37.8%±0.4%. Moreover, the curcumin beverage had a DPPH• scavenging rate of 82.86% and an $ABTS^{+}$• scavenging rate of 85.33%, exhibiting certain antioxidant activity. The curcumin concentration of the drink was 4 mg/mL, and the drink was orange, and had moderate sour and sweet taste and a typical smell of curcumin.

Comparative Example 1

In this comparative example, several control groups, respectively $Zn^{2+}$-bound curcumin, curcumin nanoparticle and pure curcumin, were established and compared with the curcumin beverage made under the optimal combination $A_3B_2C_2D_2$ in terms of sensory score, absorbance stability, precipitation rate after centrifugation, DPPH• scavenging rate and $ABTS^{+}$• scavenging rate. The change of indexes of curcumin after prepared into the beverage was investigated, and the results were shown in Table 25.

TABLE 25

Comparative experiment

| Sample | Curcumin concentration mg/mL | pH | Sensory score | Coefficient of absorbanee stability | Precipitation rate after centrifugation (%) | DPPH · scavenging rate (%) | $ABTS^{+}$ · scavenging rate (%) | Comprehensive score |
|---|---|---|---|---|---|---|---|---|
| Pure curcumin | 6.0 | 7 | 75.00 | 0.286 ± 0.180 | 0.550 ± 0.100 | 90.13 | 88.53 | 81.00 |
| $Zn^{2+}$-bound curcumin | 5.8 | 7 | 75.00 | 0.296 ± 0.200 | 0.523 ± 0.100 | 90.55 | 88.17 | 81.00 |
| Curcumin nanopartide | 4.8 | 7 | 75.00 | 0.342 ± 0.100 | 0.499 ± 0.100 | 88.77 | 86.52 | 87.40 |
| Curcumin beverage | 4.0 | 6 | 93.33 | 0.518 ± 0.120 | 0.378 ± 0.100 | 82.86 | 85.33 | 98.64 |

It can be seen from Table 25 that the DPPH• scavenging rate and the $ABTS^{+}$• scavenging rate successively decreased, while the stability increased successively in the sequence of pure curcumin solution, $Zn^{2+}$-bound curcumin solution, curcumin nano-emulsion and the curcumin drink. In addition, the curcumin was prone to precipitation in the pure curcumin solution, $Zn^{2+}$-bound curcumin solution and the curcumin nano-emulsion due to its poor water solubility is insoluble in water, which will affect the appearance. Meanwhile, the precipitated curcumin had a strong odor, which will further affect the sensory assessment. With respect to the curcumin nanoparticle, it had significantly improved water solubility, so that the beverage made therefrom had uniform system, thus achieving the highest comprehensive score 98.64.

Further, the experimental example 7 was described below to verify the anti-aging effect of the curcumin beverage provided herein.

Experimental Example 7 Anti-Aging Effect on Fruit Fly

Fruit fly was used as model, and median lethal time, average life span and maximum life span were used as indexes to evaluate the effect of the curcumin beverage on extending the life span of the fruit fly. Moreover, levels of SOD and MDA in the fruit fly were analyzed to preliminarily investigate the anti-aging mechanism of the curcumin beverage.

Preparation of *Drosophila* Medium 20 g of sucrose and 3 g of agar were dissolved in 300 mL of distilled water under stirring and boiled until the agar was completely dissolved to produce liquid A. 33 g of corn flour, 21.24 g of glucose and 4.5 g of soybean flour were dissolved in 200 mL of distilled water under stirring to produce liquid B. The liquid B was slowly poured into the liquid A, and the mixed liquid was boiled into a paste under continuous stirring. 0.125 g of paraben was dissolved with 1.25 mL of absolute ethanol and added to the paste. After cooled to about 75° C., the paste was added with 12.5 g of yeast powder, stirred thoroughly, added with 3.5 mL of propionic acid and stirred uniformly to produce the *Drosophila* medium. The medium was poured to several clean culture tubes each for 1.5-2 mL, and after the medium was completely solidified, the culture tube was invertedly placed on the operating desk for 24 h for the cultivation of fruit files.

Selection of Dose Gradient of Curcumin Beverage

Considering that the recommendation dose for humans was 0.0033 g/kg·bw·d, the daily amount of food and drinking water for a 60 kg person was set as 3000 g, based on which the experimental intermediate concentration was calculated according to the model required by the State Food and Drug Administration for health food. 1-2 concentration groups were respectively set above and below the intermediate concentration at 3-fold group interval, and a total of four dose groups were set. Moreover, one blank control group was set.

Experimental Method 300 male fruit flies and 300 female fruit flies emerged within 8 h were collected. The female and male fruit flies were distinguished by ether anesthesia. The fruit flies were randomly divided into five dose groups each consisting of 60 males and 60 females. They were placed in 2.5 cm×20 cm test tubes each for 20, and cultured at a relative humidity of 45%-75% and a temperature of 25±1° C., where the medium was replaced every four days to avoid fruit flies dying from food adhesion. The survival conditions and the number of deaths were recorded every day until all fruit flies died. The average life span, average highest life span (calculated based on the lifespan of the last ten survived fruit flies) and median lethal time were calculated for statistical analysis.

Data Analysis

The statistical analysis was performed at P<0.01 and P<0.05 using SPSS17.

Results

Influence of the Curcumin Beverage on the Lifespan of Fruit Fly

The median lethal time, average life span and average highest life span were used as indexes to evaluate the effect of the curcumin beverage on extending the life span of the fruit fly. The results were shown in Table 26.

TABLE 26

Influence of the curcumin drink on the lifespan of fruit fly

| Sex | Additive amount of the curcumin beverage (%) | Number | Median lethal time (d) | Average life span (d) x ± s | Average highest life span (d) x ± s | Average life extension rate (%) | Average extension rate of the highest life span (%) |
|---|---|---|---|---|---|---|---|
| Female | 0.0000 | 60 | 40 | 38.50 ± 6.75 | 47.80 ± 1.53 | — | — |
| | 0.0022 | 60 | 44 | 38.85 ± 7.74* | 50.04 ± 1.25* | 0.91 | 4.69 |
| | 0.0067 | 60 | 45 | 42.93 ± 4.51* | 51.10 ± 1.11* | 11.51 | 6.90 |
| | 0.0201 | 60 | 46 | 43.87 ± 7.97** | 52.01 ± 1.23** | 13.95 | 8.81 |
| | 0.0603 | 60 | 43 | 40.50 ± 9.12* | 50.20 ± 1.13* | 5.19 | 5.02 |
| Male | 0.0000 | 60 | 35 | 33.28 ± 7.32* | 43.50 ± 1.58* | — | — |
| | 0.0022 | 60 | 37 | 35.23 ± 8.45* | 45.35 ± 0.85** | 5.87 | 4.25 |
| | 0.0067 | 60 | 40 | 38.03 ± 9.23* | 47.46 ± 1.42* | 14.17 | 9.10 |
| | 0.0201 | 60 | 41 | 38.83 ± 9.77** | 48.20 ± 1.29** | 16.67 | 10.80 |
| | 0.0603 | 60 | 38 | 36.01 ± 8.20* | 45.20 ± 1.12* | 8.20 | 3.91 |

*significant at $P < 0.05$, and highly significant at $P < 0.01$.

It can be observed from Table 26 that the dose groups are significantly different from the control group in the average life span and average highest life span. The maximums of the average life span and the average highest life span were observed in the group treated with 0.0201% curcumin beverage.

In female fruit flies, the average life span and average highest life span of the 0.0201% dose group were (43.87±7.97) and (52.01±1.23) respectively, which were both higher than the control, and also significantly higher than the other groups. The life extension rates of the 0.0201% dose group reached 13.95% and 8.81%, respectively. The average highest life span of the 0.0022%, 0.0067% and 0.0603% groups was all higher than the control group. In male flies, the average life span and average highest life span of the 0.0201% dose group were (38.83±9.77) and (48.20±1.29), respectively, which were higher than the control group. The average life extension rates of the 0.0201% dose group were 16.67% and 10.80%, and the average life extension rates of the 0.0067 dose group were 14.17% and 9.10%. The average highest life span of all four dose groups was significantly higher than the control group. In addition, the 0.0201% dose group has a significant difference with the other groups in the average highest life span. Therefore, the curcumin beverage provided herein had the effect to extend the lifespan of fruit flies.

Influence of the Curcumin Beverage on the Antioxidase of Fruit Fly

TABLE 27

Influence of the curcumin beverage on the antioxidase of fruit fly

| Additive amount of the curcumin beverage | SOD (U/mgprot) | | MDA (nmol/mgprot) | |
|---|---|---|---|---|
| (%) | Female | Male | Female | Male |
| 0.0000 | 30.11 ± 1.05 | 24.2 ± 30.77 | 1.21 ± 0.25 | 1.27 ± 0.16 |
| 0.0022 | 32.11 ± 1.03* | 26.51 ± 1.22* | 0.66 ± 0.03 | 0.89 ± 0.09* |
| 0.0067 | 33.84 ± 1.52* | 28.88 ± 1.28* | 0.55 ± 0.08 | 0.59 ± 0.12* |

TABLE 27-continued

Influence of the curcumin beverage on the antioxidase of fruit fly

| Additive amount of the curcumin beverage | SOD (U/mgprot) | | MDA (nmol/mgprot) | |
|---|---|---|---|---|
| (%) | Female | Male | Female | Male |
| 0.0201 | 39.46 ± 1.12** | 30.22 ± 1.12** | 0.28 ± 0.02** | 0.32 ± 0.01* |
| 0.0603 | 32.01 ± 2.61** | 27.69 ± 0.95* | 0.35 ± 0.02** | 0.40 ± 0.05* |

*Significant at $P < 0.05$, and highly significant at $P < 0.01$.

It can be seen from Table 27 that the dose groups were significantly from the control group in the activity of SOD and the content of MDA. The activity of SOD in male and female fruit flies was improved as the addition amount of the curcumin beverage in the medium increased. When the concentration of the curcumin beverage was 0.0201%, the activity of SOD in male and female fruit flies reached the maximum. In the meantime, the content of MDA in male and female fruit flies decreased as the concentration of the curcumin beverage in the medium increased. When the concentration of the curcumin beverage was 0.0201%, the content of MDA in male and female fruit flies reached the minimum. Therefore, for female fruit flies, the 0.0201% dose group had a significantly high activity of SOD and a significantly low content of MDA than the other dose groups. In male fruit flies, the activity of SOD and the content of MDA of 0.0201% dose group differed significantly from the control group.

In the drosophlia survival experiment, the median lethal time, average life span and average highest life span of the male and female fruit flies all increased along with the increase of the addition amount of the curcumin beverage, and all reached the maximum in the 0.0201% dose group. It indicated that the curcumin beverage can extend lifespan of fruit flies, exhibiting an anti-aging effect. As the additive amount of the curcumin beverage increased, the activity of SOD increased and the content of MDA decreased. When the addition amount of the curcumin beverage was 0.0201%, the activity of SOD reached the highest and the content of MDA reached the lowest. It demonstrated that the curcumin beverage exerted its anti-aging effect by increasing the activity of SOD and reducing the content of MDA.

The disclosure is not limited to the above embodiments. It should be understood that any replacement, change and modification made by those skilled in the art without departing from the spirit of the disclosure should fall within the scope of the disclosure.

What is claimed is:

1. A curcumin nanoparticle, comprising:
curcumin as core material; and
a wall material;
wherein a weight ratio of the curcumin to the wall material is (5.5-7.5):100; and
the wall material comprises gum arabic and zein in a weight ratio of (1-5):5.

2. A method of preparing the curcumin nanoparticle of claim 1, comprising:
(1) dissolving the zein with 85% ethanol followed by magnetic stirring for 1 h and centrifugation to remove insoluble impurities to produce a zein solution; and adding the curcumin to the zein solution followed by stirring for 30 min to produce a curcumin stock solution;
(2) dissolving gum arabic with a 0.3 g/L zinc sulfate solution at 60° C. under stirring to produce an aqueous gum arabic stock solution, wherein the zinc sulfate solution is prepared by dissolving zinc sulfate with water in a water bath at 60° C., and a volume ratio of water in the aqueous gum arabic stock solution to ethanol in the curcumin stock solution is (1.5-3.5):1;
(3) adding the curcumin stock solution to the aqueous gum arabic stock solution in a trickle manner followed by stirring for 30 min to produce a curcumin nanoparticle dispersion;
(4) concentrating the curcumin nanoparticle dispersion obtained in step (3) by rotary evaporation to obtain a concentrated curcumin nanoparticle dispersion; and
(5) subjecting the concentrated curcumin nanoparticle dispersion to freeze drying to produce the curcumin nanoparticle.

3. The method of claim 2, wherein the volume ratio of the water in the aqueous gum arabic stock solution to the ethanol in the curcumin stock solution is 3:1.

4. The method of claim 2, wherein a weight ratio of curcumin to the wall material is (5.5-7.5):100, and a weight ratio of the gum arabic to the zein in the wall material is (1-5):5.

5. The method of claim 4, wherein the weight ratio of curcumin to the wall material is 7:100, and the weight ratio of the gum arabic to the zein in the wall material is 4:5.

6. A curcumin beverage, consisting of:
15% by weight of Tribute Citrus concentrate;
0.05%-0.25% by weight of xanthan gum;
0.2%-1% by weight of the curcumin nanoparticle of claim 1;
0.2%-1% by weight of starch sodium octenyl succinate;
0.05%-0.25% by weight of sodium carboxymethyl cellulose;
0.1% by weight of citric acid;
10% by weight of xylitol; and
water.

7. The curcumin beverage of claim 6, consisting of:
15% by weight of Tribute Citrus concentrate;
0.15% by weight of xanthan gum;
0.8% by weight of the curcumin nanoparticle;
0.4% by weight of starch sodium octenyl succinate;
0.15% by weight of sodium carboxymethyl cellulose;
0.1% by weight of citric acid;
10% by weight of xylitol; and
water.

8. A method of preparing the curcumin beverage of claim 6, comprising:
(1) peeling and coring Tribute Citrus fruits followed by squeezing with a juicer to produce a Tribute Citrus juice; filtering the Tribute Citrus juice twice with a double gauze to collect a filtrate; and concentrating the filtrate by rotary evaporation to a solid content of 70% to produce the Tribute Citrus concentrate;
(2) mixing the curcumin nanoparticle, starch sodium octenyl succinate and the Tribute Citrus concentrate by stirring to obtain a first mixture;
(3) homogenizing the first mixture obtained in step (2) by a homogenizer to obtain a first homogenized product;
(4) compounding the first homogenized product obtained in step (3) with sodium carboxymethyl cellulose, xanthan gum, citric acid and xylitol to produce a second mixture;
(5) homogenizing the second mixture obtained in step (4) by the homogenizer to obtain a second homogenized product;
(6) heating the second homogenized product in a water bath at 80° C. for 15 min followed by degassing to obtain a degassed product; and
(7) bottling and sterilizing the degassed product obtained in step (6) to produce the curcumin beverage.

9. The method of claim 8, wherein in step (3), the homogenization is performed at 25 MPa.

10. The method of claim 8, in step (5), the homogenization is performed at 5 MPa.

11. The method of claim 8, in step (7), the sterilization is performed at 121° C. for 10 min.

* * * * *